(12) United States Patent
Bowen et al.

(10) Patent No.: US 10,860,526 B2
(45) Date of Patent: Dec. 8, 2020

(54) SYSTEM AND METHOD OF MANAGING LARGE DATA FILES

(71) Applicant: The Regents of the University of California, Oakland, CA (US)

(72) Inventors: Benjamin P. Bowen, Berkeley, CA (US); Oliver Ruebel, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 422 days.

(21) Appl. No.: 14/091,986

(22) Filed: Nov. 27, 2013

(65) Prior Publication Data

US 2014/0164444 A1    Jun. 12, 2014

Related U.S. Application Data

(60) Provisional application No. 61/732,328, filed on Dec. 1, 2012, provisional application No. 61/827,516, filed on May 24, 2013, provisional application No. 61/962,290, filed on Jul. 15, 2013, provisional application No. 61/870,741, filed on Aug. 27, 2013.

(51) Int. Cl.
*G06F 16/11* (2019.01)
*H01J 49/00* (2006.01)
*G06F 19/00* (2018.01)

(52) U.S. Cl.
CPC .......... *G06F 16/11* (2019.01); *H01J 49/0004* (2013.01); *G06F 19/321* (2013.01)

(58) Field of Classification Search
CPC ......... G06F 17/30256; G06F 17/30705; G06F 2201/86; G06F 3/0644; G06F 3/0683; Y10S 707/913; Y10S 707/916; Y10S 707/954
USPC .......................... 707/609, 758, 821, 726, 771
See application file for complete search history.

(56) References Cited

U.S. PATENT DOCUMENTS

| | | | | |
|---|---|---|---|---|
| 6,442,518 B1 * | 8/2002 | Van Thong | ............. | G10L 15/26 704/235 |
| 7,315,849 B2 * | 1/2008 | Bakalash | .......... | G06F 17/30457 |
| 7,756,896 B1 * | 7/2010 | Feingold | ................ | G06Q 40/06 705/50 |
| 2004/0139061 A1 * | 7/2004 | Colossi | ............. | G06F 17/30592 |
| 2007/0194225 A1 * | 8/2007 | Zorn | ...................... | B82Y 35/00 250/306 |
| 2008/0152235 A1 * | 6/2008 | Bashyam | .......... | G06F 17/30153 382/224 |
| 2009/0073503 A1 * | 3/2009 | Lebaschi | ............ | H04N 1/00326 358/450 |
| 2009/0294645 A1 * | 12/2009 | Gorenstein | ........... | G06F 19/703 250/282 |
| 2009/0312817 A1 * | 12/2009 | Hogle | .................. | A61B 5/0492 607/54 |
| 2009/0318815 A1 | 12/2009 | Barnes et al. | | |

(Continued)

*Primary Examiner* — Alex Gofman
*Assistant Examiner* — Linh Black
(74) *Attorney, Agent, or Firm* — Knobbe Martens Olson & Bear, LLP

(57) ABSTRACT

Disclosed are systems and software that provide a high-performance, extensible file format and web API for remote data access and a visual interface for data viewing, query, and analysis. The described system can support storage of raw spectroscopic data such as neural recording data, MSI data, metadata, and derived analyses in a single, self-describing format that may be compatible by a large range of analysis software.

35 Claims, 19 Drawing Sheets

(56) References Cited

U.S. PATENT DOCUMENTS

| | | | | |
|---|---|---|---|---|
| 2010/0295945 A1* | 11/2010 | Plemons | ............... | B60R 1/00 348/148 |
| 2011/0047189 A1* | 2/2011 | Will | ............... | G06F 19/28 707/803 |
| 2011/0116698 A1* | 5/2011 | Weis | ............... | G06K 9/6207 382/131 |
| 2011/0182814 A1* | 7/2011 | Kelly | ............... | A61K 47/48246 424/9.1 |
| 2011/0196900 A1* | 8/2011 | Drobychev | ............... | G06F 17/30575 707/812 |
| 2011/0215235 A1* | 9/2011 | Schoen | ............... | H01J 49/26 250/282 |
| 2013/0016220 A1* | 1/2013 | Brown | ............... | G01J 3/2823 348/164 |
| 2013/0054603 A1* | 2/2013 | Birdwell | ............... | G06K 9/6224 707/738 |
| 2013/0114894 A1* | 5/2013 | Yadav | ............... | G06T 5/008 382/167 |
| 2014/0012852 A1* | 1/2014 | Kapkowski | ............... | G06F 17/30038 707/738 |

* cited by examiner

| base url | | | query string | | | |
|---|---|---|---|---|---|---|
| server url | function | dataset | selection | processing options | format | Example URL's |

```
https://openmsi.nersc.gov/openmsi/
    qmetadata/?file=20120711_Brain.h5&expIndex=0&mtype=experimentFull
    qmc/?file=20120711_Brain.h5&expIndex=0&dataIndex=0
    qslice/?file=20120711_Brain.h5&expIndex=0&anaIndex=1&x=16&format=PNG
    qspectrum/
    file=20120711_Brain.h5&expIndex=0&dataIndex=0&x=30:33&y=20:23&reduction=mean&format=JSON
    qcube/?file=20120711_Brain.h5&expIndex=0&dataIndex=0&x=30:33&y=20:23&z10:20&format=JSON
```

Python

```
1 import json
2 import urllib2
3 improt numpy as np
4 url = 'https://openmsi.nersc.gov/openmsi/qslice/?file=20120711_Brain.h5&expIndex=0
        &dataIndex=0&x=45468:45468&reduction=mean
        &format=JSON6x=45468:45468&reduction=mean'
5 ionimage = np.array( json.load( urllib2.urlopen(url)))
```

FIG. 4

SYSTEM AND METHOD OF MANAGING LARGE DATA FILES

INCORPORATION BY REFERENCE TO ANY PRIORITY APPLICATIONS

This application claims the benefit of priority under 35 U.S.C. § 119(e) of U.S. Provisional Application No. 61/732,328, filed on Dec. 1, 2012, U.S. Provisional Application No. 61/827,516, filed on May 24, 2013, U.S. Provisional Application No. 61/962,290, filed on Jul. 15, 2013, and U.S. Provisional Application No. 61/870,741, filed on Aug. 27, 2013, the entirety of which are hereby incorporated herein by reference.

STATEMENT REGARDING FEDERALLY SPONSORED R&D

This invention was made with government support under Contract No. DE-AC02-05CH11231 awarded by the U.S. Department of Energy. The government has certain rights in the invention.

BACKGROUND OF THE INVENTION

Field of the Invention

The present invention relates to systems and methods of managing and visualizing large data sets, such as neurosensory data, spectroscopic data, other types of scientific and non-scientific data, and so forth. More specifically, embodiments may include high-performance, advanced data management, model building, analysis, and visualization systems for neural recording and/or mass spectrometry imaging.

Description of the Related Art

In neurosensory analyses, neural activities from a large number of neurons can be recorded and such recordings produce a large of amount of data. The number of neurons that may be simultaneously recorded has increased in recent years. The storage of such neural recording data, as well as the high-performance retrieval, analysis, modeling, and visualization of the neural recording data, present a significant challenge. Traditional techniques are insufficient for storing, interacting, and modeling large-scale neural recording datasets. Moreover, current data file formats are insufficient for meeting such needs.

Mass spectrometry imaging (MSI) is a technology that is widely applied to image complex samples for DOE-funded program applications spanning health (Low Dose SFA), microbial ecology (ENIGMA), and energy sciences (JBEI). Unfortunately, the scale of MSI data and other types of spectroscopic data and the complexities of analyzing these large data sets present a barrier to scientists. In some cases, a single 2D-image, that may be 60 GB in size and comparison of multiple images, is beyond the computational capabilities available to most scientists. Using currently available instruments, MSI datasets with $10^6$ pixels and $10^6$ mass bins could be easily acquired, resulting in a raw file size of 4 TB.

Spectroscopic techniques such as MSI are also rapidly becoming a widespread analytical technique. In recent years, sample preparation methodologies, desorption-ionization techniques, and imaging mass spectrometry equipment have advanced to a point where standard practices can be followed yielding high quality data, and thereby enabling direct interrogation of the spatial distribution of metabolites and proteins within cells and tissues. Spectroscopic techniques such as MSI are finding widespread application in life science, bio-engineering, drug development, and studies of metabolic processes and promises to enable transformative medical diagnostics and large-scale scientific experiments.

In MSI and other spectroscopic methods, many spatially defined mass spectra are acquired across a sample. In the raw form, the data for each position is represented as a profile of intensity values over a corresponding range of mass-to-charge (m/z) values. Modern mass spectrometers are capable of resolving mass differences many orders of magnitude below the integer mass of a molecule and can accurately measure the m/z values to approximately the mass of a single electron, generating massive and highly complex datasets.

Despite numerous advances in analysis of neurosensory, spectroscopic datasets, and other types of datasets, such as MSI datasets, widespread adoption of neurosensory and/or spectroscopy analysis is hindered by a lack of fast and easy-to-use approaches for sharing, managing, accessing and provenance of raw spectroscopic data and derived analyses. While numerous open standards have been proposed for storage of neurosensory, spectroscopic data, and so forth (e g, imzML or mzML and so forth), none of the current formats efficiently support standard data access patterns, such as reading of ion images and often introduce large storage overheads. This lack in performance already at the file-format level makes visual data exploration and high-performance, complex data analysis challenging.

In current practices, spectroscopic data, such as MSI data, is sometimes binned in order to support visual data exploration in an unstructured and non-standardized way that impedes data sharing. Yet, analysis of unbinned, raw data can be important to harness the ever-increasing accuracy and resolution of mass spectrophotometry for discriminating and identifying ions. Furthermore, storage of metadata about a sample, experiment, or acquisition can be largely undefined and not managed in a structured manner. Lastly, current neurosensory and/or spectroscopic data formats, including MSI data formats, do not support storage and provenance of derived results, hindering sharing and reproducibility of analyses.

BRIEF DESCRIPTION OF THE DRAWINGS

FIG. 4 is an illustrative example of the design of an OpenMSI URL for data requests, data retrieval, and an illustrative example of an application interacting with the OpenMSI system.

SUMMARY

Figure 1A:
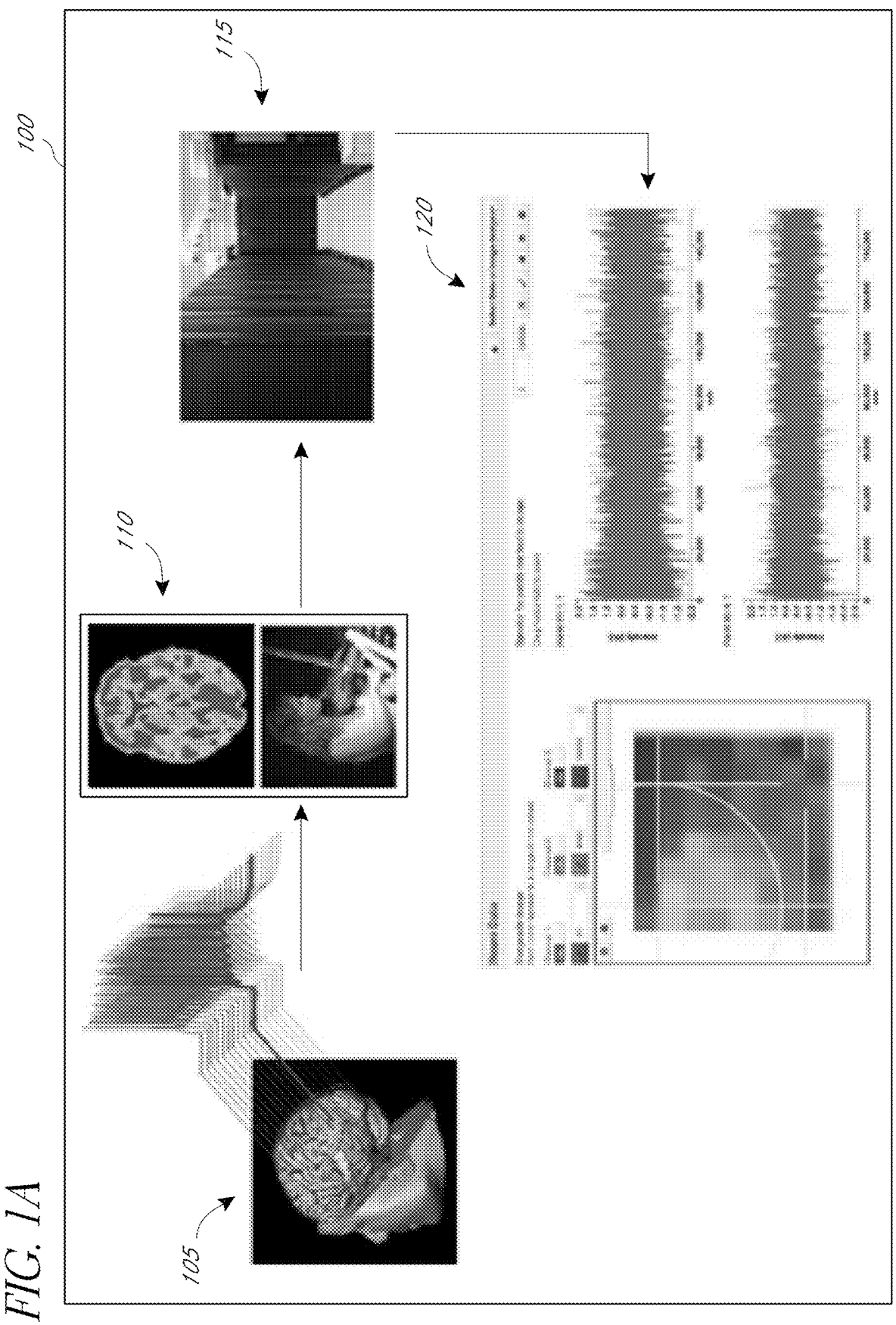
FIG. 1A illustrates one embodiment of a system for neurosensory analysis (such as neural recording) data processing.

Disclosed herein are systems for presenting neurosensory, spectroscopic, and other types of large-scale data to a user computer, the systems including: an interface to a data storage device configured to store neurosensory and/or spectroscopic data and associated metadata; a first storage module configured to store the neurosensory and/or spectroscopic data, analysis data, and the associated metadata as one or more of individual spectrally aligned data chunks, image aligned data chunks, and hybrid data chunks, wherein the stored data chunks comprises sub-blocks of the spectroscopic data; and a user interface module configured to retrieve ion image slices, spectral data, or arbitrary sub-cubes from the stored data chunks and graphically display the retrieved data and the associated metadata to the user computer.

In accordance with one aspect of the disclosure, a non-transitory computer-readable storage medium comprises computer-executable instructions that when executed direct a computing system to: store neurosensory and/or spectroscopic data, analysis data, and metadata as one or more of individual spectrally aligned data chunks, image aligned data chunks, and hybrid data chunks, and wherein the stored data chunks comprise sub-blocks of the spectroscopic data; and retrieve image slices, spectra data, or arbitrary sub-cubes from the stored data chunks and graphically display the retrieved data and the metadata to a user computer.

In accordance with another aspect of the disclosure, a computer-implemented method comprises obtaining neurosensory and/or spectroscopic data and associated metadata from an imaging device; storing the neurosensory and/or spectroscopic data and associated metadata as one or more of individual spectrally aligned data chunks, image aligned data chunks, and hybrid data chunks to a storage, wherein the stored data chunks comprise sub-blocks of the s neurosensory and/or spectroscopic data; retrieving ion image slices, spectra data, or arbitrary sub-cubes from the stored data chunks in response to a user request; and graphically displaying the retrieved spectroscopic data and metadata to a user's computer.

DETAILED DESCRIPTION

I. Introduction

Embodiments relate to data analysis software and systems for analyzing and viewing large datasets. As used to analyze and view neurosensory, spectroscopic data, and other types of large-scale data, including, e.g., neural recording data, mass spectroscopy data, and so forth, one embodiment of the system is termed herein "OpenMSI" although embodiments are not limited to only mass spectroscopy data. Embodiments of the system may also process, store, analyze, and present all kinds of neurosensory data, spectral data or spectroscopy data generated from any neural recording method and any spectroscopic method including but not limited to absorption, auger, cavity ring down, circular dichroism, coherent anti-Stokes Raman, cold vapor atomic fluorescence, correlation (several types of 2-dimensional NMR spectroscopy), deep-level transient, dual polarization interferometry, EPR, elastic scattering and reflection, inelastic scattering, inelastic electron tunneling spectroscopy (IETS), emission, energy, force, Fourier transform, frequency, hadron, hyperspectral imaging, Laser-Induced Breakdown Spectroscopy (LIBS), Mossbauer, photoacoustic, photothermal, pump-probe, Raman optical activity, Raman spectroscopy, transmission, reflectance, impedance, resonance (e.g., acoustic resonance), scanning tunneling, spectrophotometry, molecular vibration (e.g. vibrational circulator dichorism), fluorescence, nuclear magnetic resonance, thermal, infrared, atomic force, time-resolved, time-stretch, ultraviolet photoelectron (UPS), X-ray, and/or secondary emission spectroscopic methods, etc.

In addition, the OpenMSI platform is well suited for access, analysis, and visualization of large data sets from a variety of scientific and non-scientific domains. The OpenMSI system's file format, data storage and data access solutions, and data analysis functionality are suitable for interacting with large-scale scientific and non-scientific datasets. The OpenMSI's client interface, which may be based on web browsers, can quickly provide the proof of principle for many types of datasets and applications. For example, beyond the fields of mass spectrometry imaging and neural recordings, the OpenMSI system may be used to store, analyze, and/or visualize data generated from hundreds or even thousands of sensors in a damaged wetland area with records of monitored temperature, pH, salinity, and/or flow-rate, etc. Furthermore, the OpenMSI system can be used to store, analyze, and/or visualize data generated by sensors on one or more boats, for example, participating in a competition. A boat may have several thousand sensors recording everything possible at as many locations as possible on the boat.

For example, the system described herein may also be configured to efficiently access, store, and analyze data from chromatography that may or may not be coupled to mass spectrometry, spectral image data where the spectrum is determined by the wavelength of light being measured, or spectral image data where the spectrum is derived from secondary effects such as x-ray photoelectrons. Embodiments of the data analysis system platform can provide an advanced, high-performance, extensible file format and web Application Programming Interface (API) for remote data access. The system's file format may also support storage of raw spectroscopic (such as MSI) data, metadata, and derived analyses in a single, self-describing format based on the Hierarchical Data Format known as HDF5. The system's file format may also support storage of neurosensory data, including, neural recording data, metadata, and derived analyses in a single, self-describing format based on the Hierarchical Data Format known as HDF5. This format is supported by a large range of analysis software, including Matlab® and R, and programming languages, such as C++, Fortran and Python.

As discussed below, optimization of the storage layout of MSI datasets were found to accelerate common, selective data access operations by several orders of magnitude while minimizing data storage requirements. Using embodiments of the system, custom data analyses and data from other recording and/or imaging modalities can now be integrated with the selected file format and show how this new data format facilitates data provenance. Due to the ever-growing size of some datasets, particularly with large-scale datasets such as neurosensory, spectroscopic datasets, and so forth, such as MSI datasets, it is often not possible to store and analyze large datasets using locally available compute capacities. Instead, dedicated high-performance computing resources may be needed. As discussed, embodiments of this invention provide a web API that enables fast and convenient access to neurosensory, spectroscopic data, and so forth (such as MSI data), metadata and derived analysis results stored remotely. The OpenMSI system's file format, storage system, and web API enable access to neurosensory and/or spectroscopic data (such as neural recording data, MSI data, and so forth) and straightforward integration of neurosensory and/or spectroscopic technologies with modern analyses methods, web technologies and client side libraries. Optimization of data layouts in some embodiments use data chunking, compression, and data replication which were found to enable rapid data access and resulted in a greater than 2000-fold improvement in image access speed. In some cases, the OpenMSI system platform enabled data retrieval speeds of less than 0.3 seconds across the Internet, even for 50 GB-sized MSI datasets.

One embodiment includes an electronic system configured to manage and present neural recording data and/or mass spectrometry imaging data to a user's computer. One aspect of the system is an interface to a data storage configured to store neural recording data and/or mass spectrometry imaging data and associated metadata. It should be realized that this interface may be a direct connection to the data storage, or an indirect interface, such as through the Internet or other wide area or local area network. The electronic system may also include a first storage module configured to store the received neural recording and/or mass spectrometry imaging data and metadata in one or more of spectrally aligned data chunks, image aligned data chunks, and hybrid data chunks. In some embodiments, data chunks are sub-blocks of spectrometry imaging data. In addition, the system may include a user interface module configured to retrieve ion image slices, m/z spectra data or arbitrary sub-cubes from the stored data chunks and graphically display the accessed neural recording and/or mass spectrometry imaging data and metadata to the user.

The OpenMSI file format, file and analysis API and Web API, build the foundation of an OpenMSI science resource. In some embodiments, all software components of the system may be implemented in Python using the h5py library to interact with HDF5 and using the Django web application framework for web-related tasks. However, it should be realized that embodiments of the invention are not limited to any particular software format or programming language. In some embodiments, the OpenMSI system includes a storage module that uses a new file format for storing raw large scale datasets, such as neurosensory, spectroscopic data (such as MSI data) and so forth, derived analysis, and metadata in a single file using a portable, efficient, parallel, self-describing file format based on HDF5.

Also, in some embodiments, the OpenMSI system can include a user interface module with an API that interacts with the file format and describes the optimization of the data-layout using chunking, compression, and data duplication to accelerate the most common data access operations and to reduce storage cost. The OpenMSI system may also include interfaces and modules including an easy-to-use web-based API for accessing large scale datasets, such as neurosensory, spectroscopic data (such as MSI data, neural recording data) and so forth and derived analyses stored remotely via the web. Finally, the OpenMSI system can include interfaces and modules, including an API that facilitates the integration of custom data analyses with the OpenMSI file format and web API. Overall this OpenMSI platform addresses many of the data challenges to large scale data analysis such as neurosensory, spectroscopic data (such as MSI data) and so forth, by making advanced, high-performance data analysis and computing easily accessible to neuroscience and spectroscopy scientists, by enabling fast sharing and access to raw MSI data and other neurosensory and/or spectroscopic data and derived analyses via the web (see, e.g., FIG. 1).

II. MSI Data and Analysis Requirements

FIG. 1A illustrates one embodiment of a system 100 for neurosensory data (such as neural recording) processing. In some neurosensory analyses, neural recordings 105 may be represented in a manner that is analogous to a 3-dimensional image. A coordinate (e.g., pixel) may be used to record from one or more neurons. The neural recording 105 is analogous to spectra, and is in fact a time trace of electrical activity 110 at that location. Because the physical location of the neural recording is known, a neural recording 105 of electrical activity 110 at a plurality of positions may be done and represented as an image of electrical activity at one or more points in time.

In some embodiments, more than one type of sensory devices may be used at each position. These devices can measure electrical, photonic, and biochemical data. Consequently, the recordings at a given position could contain many neural recordings data and even spectral data. In addition, these recordings may be taken in concert with many other observations including sensory motor control, gross-neural activity, motion, activities, thought, and many other phenomena.

According to some embodiments, the neural activity recording data may be transferred to a remote data center 115 and integrated into the OpenMSI system and its omsi fileformat. The OpenMSI system's data access and data storage solutions provide efficient means to return time-traces and spectra at one or more positions. Likewise, the OpenMSI's data storage and data access solutions can also provide efficient return of the spatial "image" of activity at a given data slice. Moreover, these results may be presented to a user in a web-browser 120 through graphical displays that are highly interactive. This highly interactive user experience is a significant improvement over the traditional data visualization approaches for neurosensory data, which are usually slower and less interactive.

Figure 1B:
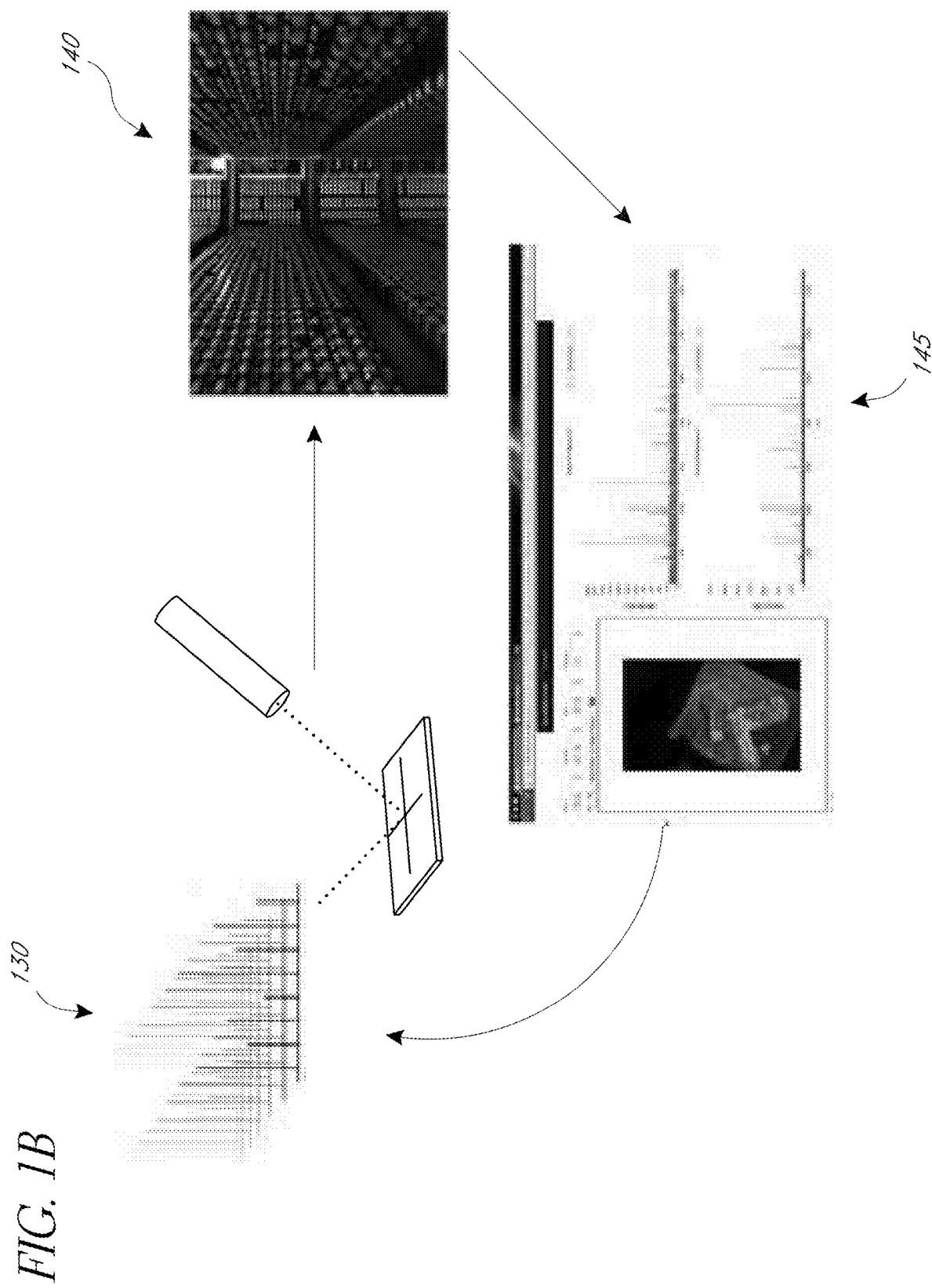
FIG. 1B illustrates one embodiment of a system for spectroscopic (such as mass spectrometry imaging) data processing.

FIG. 1B illustrates one embodiment of a system for spectroscopic data (such as mass spectrometry) processing. In some embodiments, spectroscopic data 130, such as MSI data, may be acquired at a lab and transferred for more processing and data storage. Raw spectroscopic data and derived analysis results may be visualized and further analyzed via the web using an interactive web interface. 145. As shown in FIG. 1B, a mass spectrophotometer is used to desorb and ionize molecules and generate spectra. The spectroscopic data 130 from the mass spectrophotometer is transferred to a large capacity data storage site 140 for later analysis. Once the data is stored in the proper format the data storage site 140, such as the National Energy Research Scientific Computer Center (NERSC), it can be made available through the OpenMSI system to Internet browsers for rapid evaluation by scientists. In some other embodiments, other types of large-scale data from other external data sources may also be acquired and analyzed using the data storage, access, and analysis framework described herein. For example, the system described herein may also be configured to efficiently access, store, and analyze data generated by absorption, emission, energy, frequency, and/or secondary emission. The system described herein may also be configured to efficiently access, store, and analyze data from chromatography coupled to mass spectrometry and or other spectroscopic methods.

However, storage and management of neurosensory and/or spectroscopic data (such as MSI data) is challenging; the data is extremely large, shows large differences between spatial and mass resolution (three to four orders of magnitude), and may require fast orthogonal accesses to spectra and ion images. A 2D MSI (or other spectroscopy) dataset can be described as a three-dimensional cube of (x,y,m/z). Current 2D raw MSI (or other spectroscopy) datasets contain spectra from hundreds of thousands of positions with each position containing one or more spectra. Each spectrum, describes the distribution of masses at a given image location (pixel) and typically consists of $10^5$ to $10^7$ integer intensity values. Using currently available instruments, neurosensory and/or spectroscopic datasets (e.g., MSI datasets) with $10^6$ pixels and $10^6$ mass bins could be easily acquired, resulting in a raw size of 4 TB.

In practice, large-scale data, such as neurosensory data, spectroscopic data (such as MSI data) and so forth, is typically used in a write-once read-many fashion, i.e., the data is written once during data acquisition and read repeatedly during the visualization and analysis process. For instance, many visualization and analysis algorithms do not process the full neurosensory and/or spectroscopic data cube (such as MSI data cube) at once but rely on repeated selective read of: i) spectra, ii) ion-images, and iii) arbitrary 3D subsets of the data.

Analysis of complex neurosensory and/or spectroscopic datasets (such as MSI datasets) is challenging and is commonly based on highly complex and interconnected analysis pipelines consisting of various data pre-processing (e.g., background correction), data reduction (e.g., peak finding), data integration (e.g., peak image computation), dimension reduction (e.g., PCA or NMF), and feature detection and clustering steps (e.g, kmeans). Making advanced data analyses easily accessible to non-expert users can facilitate widespread use of MSI and other neurosensory and/or spectroscopic methods.

Finally, to facilitate distributed, inter-disciplinary, collaborative analyses of neurosensory and/or spectroscopic data and to enable the scientific community to share and benefit from results from MSI and other spectroscopy techniques, researchers may be able to share data and analysis results with other researchers around the world and the MSI and spectroscopy community at large. An appropriately designed file format, such as that described herein, is self-describing, platform independent, and easily accessible via a large range of programming languages and analysis systems.

III. OpenMSI File Format and API

In some embodiments, the OpenMSI system may include a custom file format that is an extensible, portable, self-describing, and parallel-aware neurosensory and/or spectroscopic data (such as MSI data) file format based on HDF5. HDF5 is a suite of technologies, consisting of a versatile data model, portable data format, and a widely accessible software library and API, which include a rich set of integrated features for optimization of I/O performance and tools for managing, viewing and manipulation of HDF5 data collections. In some embodiments, OpenMSI files may define valid HDF5 files so that the standard HDF5 APIs and tools can be used to interact with OpenMSI (also referred to as "omsi") files. This allows extensibility of the OpenMSI system's format. In some other embodiments, file formats other than HDF5, including other data storage system (e.g., database systems) and combinations thereof, may be used or customized by the OpenMSI system to achieve flexible and structured large-scale data storage capabilities.

Portability of the OpenMSI system's format means that OpenMSI files can be used directly without change on architectures and operating systems for which HDF5 is available. HDF5 is available for Windows and Unix-based systems—including Linux and MacOS—and well-supported HDF5 APIs exist for common programming languages, e.g., C, C++, Fortran, or Python, and many advanced visualization and analyses systems, such as, Matlab® and R, support HDF5 natively. Self-describing of the OpenMSI system's format means that all information about the data hierarchy, data types, etc. are directly encoded in the HDF5 files so that a user can, without prior knowledge about the file, explore the file hierarchy and load data similar to how one browses files and directories on a file system.

In the following we now first describe how data is organized in the OpenMSI data format according to some embodiments of the disclosure. In some other embodiments, the portability of the OpenMSI system may mean that the OpenMSI files and its cross-platform compatibility can be achieved with using the HDF5 format. Instead, other file formats or systems may be used to store large scale data such as neurosensory, spectroscopic data, and so forth, such as MSI data.

In HDF5, data may be stored as multi-dimensional data arrays. HDF5 supports a large range of standard data types as well as complex user-defined compound data types. Similar to directories in file systems, datasets can be organized via so-called groups in HDF5. In addition, according to some embodiments of this disclosure, groups and datasets may be assigned additional attributes. Attributes can be metadata objects describing the nature and/or intended usage of a primary data object, e.g., dataset or group. In some embodiments, instead of multi-dimensional data arrays, another data structure may be used to store the neurosensory, spectroscopic data, and so forth, such as MSI datasets.

Figure 2:
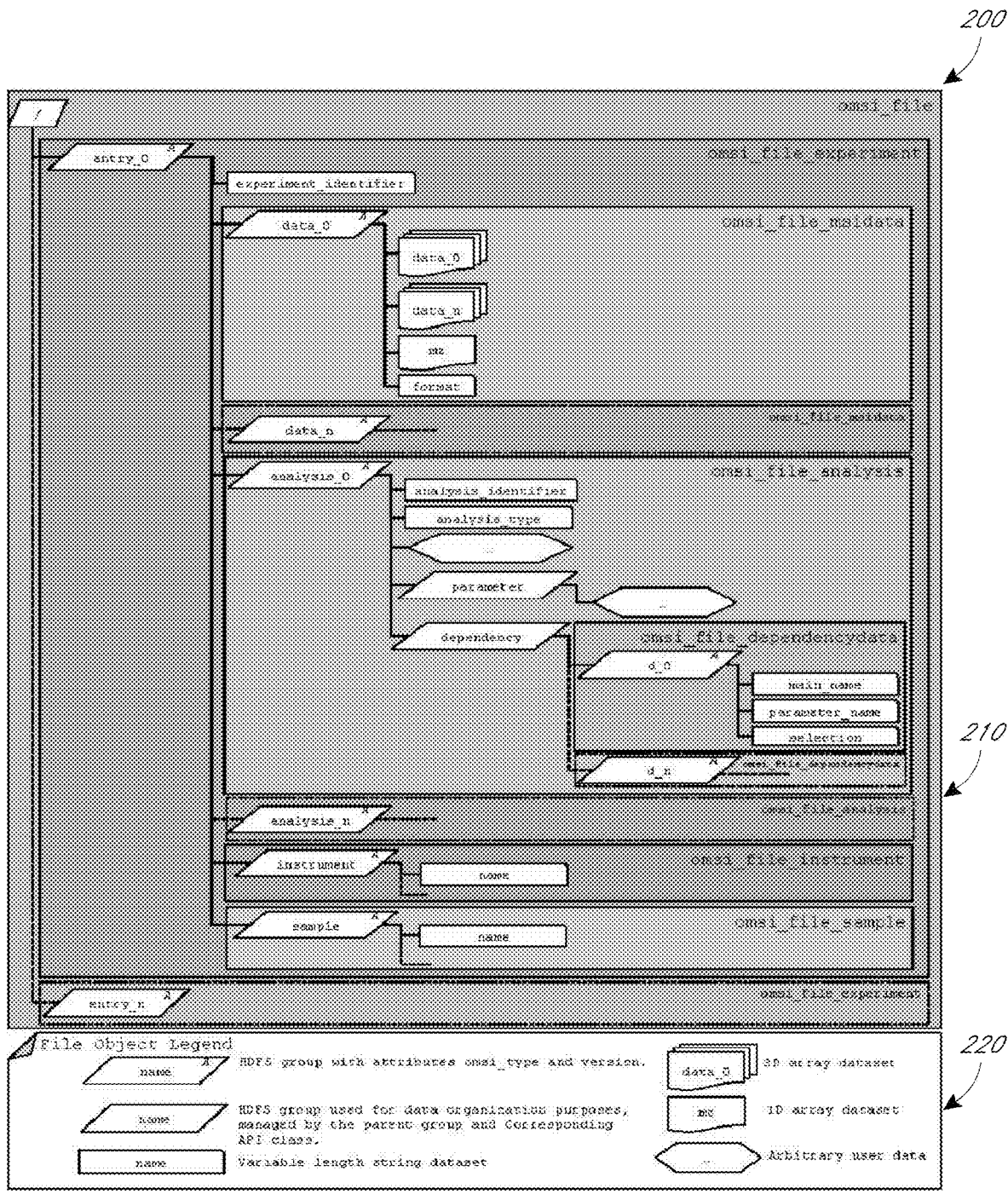
FIG. 2 illustrates one embodiment of an overview of the OpenMSI file format hierarchy.

FIG. 2 describes a file object embodiment 200 according to the disclosure, showing a storage module 210's organization of raw neurosensory, spectroscopic data, and so forth, such as MSI data, metadata, and derived analyses via groups and datasets in OpenMSI HDF5 data files. In some embodiments, OpenMSI files contain a root group. Data associated with a particular imaging experiment may then be stored in a corresponding /entry_# group. This allows for convenient storage of data from multiple related experiments in a single OpenMSI file. Each /entry_# group may contain a simple string dataset /entry_#/experiment_identifier used to name and uniquely identify the experiment. Metadata describing the instrument and sample associated with the experiment may then be stored in separate /entry_#/instrument and /entry_#/sample groups. Since the HDF5 format is self-describing, custom metadata may be added to the sample and instrument groups without violating the OpenMSI file format. Raw neurosensory, spectroscopic data, and so forth, such as MSI data and derived analysis results may then be stored in dedicated /entry_#/data_# and /entry_#/analysis_#. This data organization allows the OpenMSI system to store an arbitrary number of raw neurosensory, spectroscopic datasets, and so forth, and derived analyses for each experiment represented by a /entry_# group. Other strings and names may also be used to represent the organization of the storage module 210. Moreover, in some other embodiments, the hierarchy of the strings, for example, the sequence of "entry," "experiment-identifier," and "analysis", etc., may be different. The File Object Legend 220 illustrates various types of datasets and symbols representing each type of dataset as shown in FIG. 2.

The OpenMSI file format API then follows an object-oriented design that models the group hierarchy of the file format. In some embodiments, each main HDF5 group is represented in the API by a corresponding class responsible for creation, management, and access of the corresponding HDF5 group type. In some embodiments of the disclosure, groups with a corresponding API class are referred to as managed groups. The class type that may be used to access a particular group can be uniquely determined based on the naming scheme describe above or a similar naming scheme. In some embodiments, optional HDF5 attributes are associated with all main groups to indicate the interface class and version number of the class that should be used to interact with the group to achieve increased flexibility and extensibility of the file format.

According to some embodiments of this disclosure, raw neurosensory, spectroscopic data, and so forth, such as MSI data, may be stored in a /entry_#/data_# group rather than directly in an HDF5 dataset, which provides the OpenMSI system with great flexibility with respect to the data layout and storage of additional associated datasets. For example, in the embodiment where the raw data defines a complete 3D MSI data cube (or other 3D neurosensory data cube, spectroscopic data cube), each data # group contains i) a string dataset data_#/format indicating the data format used, ii) a 1D floating-point array data_#/mz with the m/z values for the spectrum dimension and iii) a 3D array data_#/data_# with the 3D MSI data cube (or other 3D neurosensory and/or spectroscopic data cube). This design provides the OpenMSI system with great flexibility in that the OpenMSI system can organize neurosensory, spectroscopic data, and so forth, such as MSI data in different formats (indicated by the data_#/format string) optimized for different practical cases.

In some other embodiments, for example, to avoid possibly large storage overheads by storing an uncompressed, full 3D cube even if only a small region of interest has been imagined, the particular embodiment of the OpenMSI file API may support storage of mass spectra as a 2D datasets of spectra along with additional small index datasets to record the relationship between spatial (x,y) locations and spectra. The embodiment of the OpenMSI file format and API enables the OpenMSI system to flexibly extend the OpenMSI system and its file format to accommodate other optimized large scale data storage formats, as well as to integrate data from other imaging modalities, such as, light microscopy. Organizing raw neurosensory, spectroscopic data, and so forth such as MSI data in an HDF5 group, allows the OpenMSI system to also store multiple copies of the same data as numbered instances of data_#/data_# datasets. As described herein, multiple copies of the same data may be stored in the OpenMSI system, and using different data layouts can significantly accelerate orthogonal selective data accesses.

As illustrated in FIG. 2, in some embodiments, the OpenMSI system's file format and API may follow the same semantic hierarchy to enable fast and efficient file processing, storage, and retrieval. Each main HDF5 (or any other format) group may be managed in a file format API by a corresponding class responsible for providing access to and creating the direct content of the group in the file.

According to some embodiments of this disclosure, the omsi_file_msidata interface class is designed to provide convenient access to raw MSI data independent of the data format used. In some embodiments, the class provides an array-based interface which allows a user to interact with the data as a 3D data cube independent of whether the large-scale data, such as a MSI dataset, is stored as a full 3D cube or in a reduced data format. In cases that multiple copies of the same dataset are available, the interface also automatically determines the data copy that is best suited to resolve a given data request. In some other embodiments, the interface class is designed to provide a convenient interface to other data structure or data storage schemes besides array-based interfaces, such as hash-table based interfaces, etc. Providing a consistent data interface, independent of the underlying storage format, significantly simplifies the access to the data and eases development of data analysis algorithms. At the same time, the omsi_file_msidata interface may also allow the developer to directly access all datasets stored within the corresponding data_# group, enabling development of optimized algorithms that are designed to take advantage of different data organizations.

Data stored in /entry_#/analysis_# groups, describing derived analysis results, may also be managed by instances of the omsi_file_analysis API class. Depending on the embodiment, an analysis group may contain: i) a string dataset analysis_identifier used to name and uniquely identify the analysis, ii) a string dataset analysis_type indicating the analysis class that was used to compute the analysis, iii) a group for storing user defined analysis parameters, iv) a group for storing analysis dependencies, and v) an arbitrary number of datasets with analysis results. The omsi_file_analysis interface class is designed to allow the developer to easily store and retrieve custom analysis data without having to know the underlying data file format. As disclosed herein, to store and retrieve custom analysis data, the developer/user simply needs to provide an instance of the omsi_analysis_base analysis API class to omsi_file_analysis, which in turn handles storing the analysis data, parameters and dependencies in the OpenMSI file as well as restoring of the data from file.

A. Data Provenance

Data provenance provides a historical record of data and its origins by documenting the inputs, entities, systems and processes that influence data of interest, providing critical evidence to study data dependencies, detect and recover errors and auditing of analyses.

Figure 3:
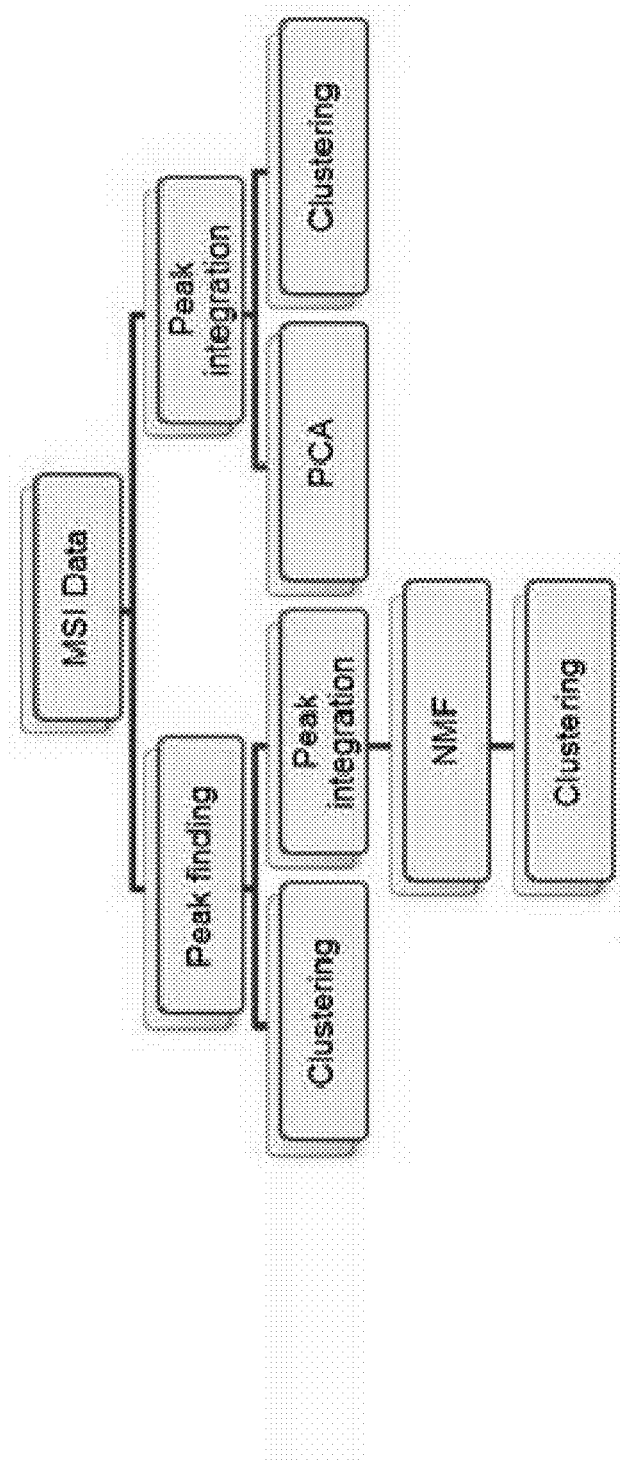
FIG. 3 is a diagram illustrating one embodiment of a data provenance graph for spectroscopic (such as mass spectrometry imaging) data.

FIG. 3 is a diagram illustrating one embodiment of a data provenance graph for mass spectrometry imaging and/or other types of large-scale data. In order to reproduce derived analysis results, a user needs to be able to retrace how the analysis was performed and how it depends on previous analysis steps. Depending on the embodiment, for an analysis, the OpenMSI system may store in the HDF5 file: i) the output of the analysis in a managed group /analysis_#, ii) all input parameters in a dedicated group /analysis_#/parameter and iii) dependency information in a dedicated group /analysis_#/dependencies. For a dependency, the OpenMSI system may store the name of the dependent input parameter, the path to the corresponding managed group (or HDF5 dataset), and if only parts of the dataset were used in the analysis, the corresponding selection. The OpenMSI system stores and manages dependency information directly in the file format and API, rather than using HDF5 hard or soft links, because this mechanism makes the dependencies explicit and allows for flexible extension of dependencies with additional information in the future. Using this approach, the OpenMSI system can reconstruct for each analysis all its inputs and direct dependencies on prior analysis or raw neurosensory, spectroscopic datasets, and so forth, such as MSI datasets. This information is sufficient to reconstruct the complete analyses tree for a given experiment, describing all analyses and MSI datasets (nodes) and their inter- (edges) (see, e.g., FIG. 3).

Data provenance is important not only for derived analyses but also for raw MSI data. As described in the previous section, for experiments, the OpenMSI system can store a diverse set of metadata information in the instrument and sample groups, describing how the raw neurosensory and/or spectroscopic datasets (such as MSI datasets) were acquired. In some embodiments, besides traditional metadata information in the instrument and sample groups, other metadata from other sources, for example, in cases where data has been transferred in from an outside data source, the name/origin/experiments involved in the outside data source, may also be kept and stored. In cases where different large-scale (such as MSI) datasets associated with the same experiment have been acquired using different instruments, the OpenMSI system may optionally include separate instrument and sample groups as part of the large-scale data groups, such as neurosensory/spectroscopic data storage groups, and so forth, i.e., data_# (not shown in FIG. 2). This may be important, for example, in the case of MSMS experiments (or other experiments regarding neurosensory, spectroscopic data, and so forth) in which secondary diffraction mass spectra are acquired for select ranges of the primary mass spectra of a sample. In this case the OpenMSI system may generate additional data_# storage for each unique refined m/z range. Similar to derived analyses, the OpenMSI system may, in some embodiments, document the dependencies between the secondary neurosensory and/or spectroscopic data groups and the primary neurosensory and/or spectroscopic data via additional data_#/dependencies storage groups.

B. Data Layout Optimization

In some embodiments, while HDF5 natively supports multi-dimensional arrays, on disk the data is linearized to a 1-dimensional data stream. The data layout describes the strategy by which the data is linearized. Traditional binary formats typically simply flatten the large-scale data, such as neurosensory data, spectroscopic (such as MSI) data, and so forth, into a single monolithic block on disk by storing the neurosensory and/or spectroscopic (such as MSI) data one spectrum at a time. These types of data layouts, in which the entire data is simply serialized into a monolithic block on disk that maps directly to a memory buffer of the size of the datasets, are typically referred to as contiguous data layouts. The traditional one-spectrum-at-a-time continuous data layout may be well suited to access single full spectra but shows very poor performance for access of ion images (see e.g., FIG. 10 and discussions herein). However, to achieve optimal performance for the typical selective read operations on large-scale data, such as neurosensory, spectroscopic data (such as MSI data), and so forth—i.e., read of spectra, ion images and subcubes—, the OpenMSI system's file format and APIs support a number of data layout optimizations, including chunking, compression and data replication, described in detail in the following paragraphs. The effectiveness of these various data layout optimizations are evaluated hereinafter. In some embodiments, data layout optimizations may be implemented transparently for the user directly by HDF5 (chunking and compression) and the omsi_file_msidata API (data duplication), allowing the user to interact with the data in a consistent manner, independent of the data layout used to store the data on disk. In some other embodiments, one or more of the data layout optimization techniques described here may be used alone or in combination with other types of data layout schemes too.

Accelerating Selective Data Access Operations using Chunking. Chunked data layouts are an alternative to the traditional contiguous data layouts. Using data chunking the data is split into multiple independent sub-parts—so called, chunks—which are stored separately in the file. A stored data chunk may include sub-blocks of the mass spectrometry imaging data of various sizes and dimensions. Selection of an optimal size and dimension is discussed herein. In HDF5, chunks can be stored in any order and at any position within an HDF5 file. Individual chunks (sub-blocks of the neurosensory data, spectroscopic data, and so forth) can then be written and read independently, which allows for improved I/O performance when operating on subsets of the data. Since chunks are independent of each other, this strategy also allows for efficient parallel data read and write. Using chunking, the OpenMSI system may optimize the data layout to enable fast access to select portions of the data while avoiding traversal of data portions not needed for a given selective data access. Which chunked data layout may be the best may depend in practice greatly on the data access patterns that need to be optimized Considering the most common access patterns in MSI and other types of methods of accessing neurosensory data, spectroscopic data, and so forth, the OpenMSI system may consider the following three main chunking strategies: i) spectra aligned chunking, i.e., store a single full or partial spectrum per chunk, ii) image-aligned chunking, i.e., store a single full or partial ion-image per chunk, and iii) hybrid chunking, i.e., store a 3D subcube describing a subset of multiple spectra and ion-images (see e.g., FIG. 11 and discussions herein). Depending on the embodiment, additional chunking strategies may also be implemented in the OpenMSI system.

Reducing Storage Cost and Accelerating I/O Using Compression.

For chunked data layouts, HDF5 allows the data—i.e., the individual chunks—to pass through user-defined filters while being written to or read from disk. Multiple such I/O filters may be applied and arranged in a pipeline fashion, while all filters are applied transparently and automatically by the HDF5 library whenever necessary, allowing the user to interact with the data in a consistent manner independent of which I/O filters are applied. According to some embodiments of this disclosure, the OpenMSI system may use compression filters with the goal to reduce storage cost and to accelerate data read operations by reducing the amount of data needs to be transferred via the system bus and network. HDF5 provides a number of different compression filters, including gzip (deflate), szip, and LZF compression. While gzip is available by default as part of HDF5, the szip and LZF compression filters rely on optional external compression libraries and may not be available with all standard installations of HDF5. To ensure broad applicability of the omsi file format, the OpenMSI system, may focus on the use of standard gzip compression. Gzip defines a lossless compression scheme, i.e., no information is lost in the compression process. In some other embodiments of the system other compression filters (including szip, LZF, and others) may be used as well.

Accelerating Orthogonal Data Accesses Using Data Replication:

Linearization of the data on disk makes it impossible to achieve optimal performance for orthogonal data access operations, here access to spectra and ion images. In some situations, data layouts that are optimal for access of spectra may not be optimal to allow efficient access to ion images and vice versa. While it may seem undesirable at first sight, replicated storage of MSI data and/or other types of large-scale data (such as neurosensory data, spectroscopic data, and so forth) using different optimized data layouts can significantly improve selective read performance, improve responsiveness of interactive applications, and substantially reduce the compute cost for parallel data analyses. Support for replicated data storage may be implemented transparently in the OpenMSI file API through the omsi_file_msidata interface, which allows analysis-codes to interact with the data as a single, regular MSI dataset. In cases that multiple copies of a dataset exist, the API automatically selects the dataset that is most efficient to resolve a given data request and retrieves the data. In some embodiments, two copies of the data may be stored, one optimized for access of spectra and one optimized for access of ion images. Even when storing the data twice, the resulting compressed MSI HDF5 files are in practice still substantially smaller (typically half the size or less) than the original raw binary data. In other embodiments, more or less number of copies of a dataset may be stored and used by the OpenMSI system. Further, the system may use a variety of methods to determine the best cop(ies) of the dataset that is most efficient, among all the available replicated copies. The OpenMSI system may do so based on a variety of considerations, including but not limited to whether the required data is local or stored remotely, the type of data requested, the storage layout of the different data copies, and where the user is located, etc.

WEB API:

The primary goals during the design of the OpenMSI web API have been simplicity and usability. One primary objective has been to the efficiently support exploratory analyses of the data via the web while the computationally intensive analyses are executed on high-performance computing resources (e.g., such as the National Energy Research Scientific Computing Center ("NERSC")). Most data analyses are based on the following three data access pattern: i) read spectra; ii) read ion-images; and iii) read arbitrary subcubes of the data. While the underlying MSI datasets (or other datasets of neurosensory data, spectroscopic data, and so forth) are large, the data required during individual data requests required for data exploration may typically be small.

The OpenMSI system may include a user interface module. The user interface module may contain one or more OpenMSI web APIs. FIG. 4 is an illustrative example of the design of an OpenMSI URL for data requests, data retrieval, and an illustrative example of an application interacting with the OpenMSI system. In some embodiments, the OpenMSI web API includes five functions—qmetadata, qmz, qslice, qspectrum, and qcube—which may provide highly-efficiency access to the data, including metadata and raw MSI (and/or other types of neurosensory data, spectroscopic data, and so forth) and derived analysis data. Depending on the embodiment, other functions may be implemented to provide high-efficiency access to the data. URL patterns may be effectively encoded to interact with data. (see, e.g., FIG. 4).

The qmetadata call may be used to retrieve metadata information about which files are available on the server and which information is available in the files.

The qmz call may be used to retrieve information about the m/z data axis. Information about the m/z axis is typically frequently reused. To avoid large overheads due to repeated transfer of the m/z data, the OpenMSI system may separate this information into an independent call that may be executed once at the beginning of any analysis.

In some embodiments, the qslice, qspectrum, and qcube patterns may provide easy-to-use support for the three most common selective access patterns, i.e., read ion image slices, read m/z spectra and read arbitrary subcubes of the data. To minimize the amount of data that needs to be transferred via the web, all access patterns support common data reduction operations—including maximum, minimum, average, standard deviation, variance etc.—which are applied on the server prior to transfer of the data. This allows one to conveniently access, e.g., maximum projection ion-images of selected m/z ranges or mean spectra for arbitrary sets of spectra, while only the final image or spectrum needs to be transferred via the web. Further detailed descriptions of the five URL patterns are provided herein with regard to the OpenMSI Web API URL patterns.

In some embodiments according to this disclosure, the web API may be implemented in Python using the Django web application framework and as the file format, the web service is cross platform compatible. In other embodiments, the web API may be implemented using other languages and systems. In one embodiment of the web API, the system may transfer all data either as easy-to-use JSON objects or as images (e.g., ion-images of curve plots of spectra). To also support efficient retrieval of larger subsets of MSI datasets (and/or other types of neurosensory and/or spectroscopic datasets), the system may also support retrieval of data directly in binary HDF5 or other format.

IV. Analysis API

To make use of new algorithms developed by the very active MSI community, the OpenMSI system provides a dedicated analysis API designed to ease integration of custom analyses algorithms with OpenMSI. The basic analysis API may consist of a set of base classes, which in concert enable direct integration of new analysis with the OpenMSI system file format and web API. In some embodiments according to this disclosure, the main interface class relevant to the analysis developer is omsi_analysis_base, which is disclosed herein too.

Integrating Analyses with the OpenMSI File Format.

To integrate an analysis with the OpenMSI file format, the developer simply needs to specify all parameter data, analyses output and data dependencies in three Python dictionaries defined in the analysis base class omsi_analysis_base. For the parameter and analyses data, a dictionary entry may require three fixed keys to be specified for the data entry describing the name, type and the data object to be stored. For dependencies, the system may, depending on the embodiment, require that the developer specifies the name of dependent parameter, the name to be used in HDF5, and the OpenMSI file object the parameter depends on. Once the developer has entered the relevant data into the dictionaries, the analysis can be added to OpenMSI HDF5 files simply by providing the specific instance of the derived omsi_analysis_base object as input to the omsi_file_experiment.create_analysis( . . . ) function. All analysis data, parameters and dependencies are then automatically stored to the current file in compliance with the OpenMSI file format specification and a new omsi_file_analysis object is created to enable direct interaction with the newly create managed analysis group. In other embodiments, different information or different combinations of information may be stored to represent dependencies, analysis parameters, analysis data and other analysis-related information The omsi_analysis_base and omsi_file_analysis then also provide the functionality needed to restore all analysis data from file. The OpenMSI system provides a user here with the option to flexibly access individual data fields as well as to retrieve a new instance of the corresponding analysis class used to generate the analysis results with all stored data fields populated as specified in the data, parameter and dependencies dictionaries during the save process. In practice, the default analysis file format interface functions may be sufficient to support common analysis use cases required for implementation of, e.g., per-spectrum peak analyses, peak integration, dimension reduction, or clustering algorithms etc. To flexibly support also more specialized use cases, in some embodiments, the omsi_analysis_base class provides a set of dedicated, custom read/write functions, which a developer may overwrite in order to implement custom read/write functionality. These custom functions may be invoked by the standard analysis file format interface functions so that all default behavior is handled automatically while the developer may only needs to describe analysis-specific extension to the standard file format. In some embodiments of the OpenMSI system, the custom functions may be further extended by a developer or a user of the OpenMSI system to include more functionalities beyond the default ones. The customized functions are supported through OpenMSI's transparent and platform independent environment.

Integrating Analyses with the OpenMSI Web API.

If the names of all relevant analysis-related datasets in the HDF5 file are known, then all data can be directly accessed using the standard URL patterns. In order to allow the analysis developer to quickly provide effective visualizations of analysis results to the user without requiring the user to know anything about the analysis itself, the OpenMSI system allows the developer to define custom interfaces for the qmz, qslice, and qspectrum URL patterns simply by overwriting corresponding functions provided by omsi_analysis_base. The developer here only needs to implement the actual data load, while all other operations—e.g., parsing of URL parameter, data reduction, formatting of the data output, etc.—are handled by the OpenMSI software stack. In many cases, one needs to be able to provide multiple different ways in which images or spectra can be computed from an analysis. In some embodiments, the OpenMSI system's Web API supports this need by allowing the user to specify an optional, integer viewerOption parameter in the URL string. The analysis developer here may need to provide a list describing the different options available for the qslice, and qspectrum URL patterns. Depending on the embodiment, the default implementations of the qmz, qslice, and qspectrum URL patterns in omsi_analysis_base may be designed to resolve all direct and indirect dependencies of the analysis. Using the default implementation, the OpenMSI system can directly expose all prior data the analysis depends on via the analysis specific qmz, qslice, and qspectrum URL patterns so that the analysis developer can focus on the implementation of visualizations for the current analysis while visualizations for all analysis dependencies are directly available to them. Via the abstraction provided by the qmz, qslice, and qspectrum URL patterns, the OpenMSI system can easily integrate new analysis with clients based on the OpenMSI WebAPI. Since the URL patterns (qmz, qslice, and qspectrum) remain the same for all analysis, and no additional implementation effort is required on the client side as new analyses are made available as part of the OpenMSI system's file format and web server. In some other embodiments, the default implementations of qmz, qslice, and qspectrum URL patterns may be extended or further customized based on the user's needs.

Coupling Different Analyses.

Raw MSI datasets (neurosensory data, spectroscopic data, and so forth) and derived analysis data are accessed using an array-based interface similar to the standard Numpy and h5py array syntax. This basic concept allows integration of different analysis algorithms in a pipeline fashion to, e.g., first compare a global peak matrix from the raw data followed by a dimensions reduction and data clustering. Dependencies to any prior analyses can then be tracked simply by providing the corresponding h5py file object or OpenMSI file API management objects (e.g., omsi_file_msidata or omsi_file_analysis) as additional analysis inputs.

V. Web-Based Data Exploration

Based on the OpenMSI web API, the OpenMSI system can support an interactive web-based, HTML5 viewer application. Using this viewer, a user can interactively define ion-images and select spectra to be displayed. Ion-images may then directly be retrieved from the complete, raw MSI data (neurosensory data, spectroscopic data, and so forth) during each data request. As disclosed in this embodiment, using OpenMSI system's new data format and web API, the OpenMSI system can resolve these data requests in less than ~0.25 s via the web even for large MSI datasets and/or other types of neurosensory data, spectroscopic data, and so forth. In some embodiments, the viewer may use the standard URL patterns without any knowledge about the specific names of datasets or organization of the data in the HDF5 files. The web client is in this way isolated from any specific implementation details on the server end and can flexibly display images and spectra for raw data and all derived analyses and their dependencies. Being able to view data from dependencies of an analysis is important because, for example, in the case of dimension reduction algorithms one often wants to view derived images of selected components of the dimension reduction while viewing spectra plots of the loadings vector or from the raw data used to generate the analysis. Although the words "Web-Based" are used here, in some embodiments, the same data exploration may be made available through applications such as mobile device applications, desktop applications, with or without an internet connection.

Figure 8:
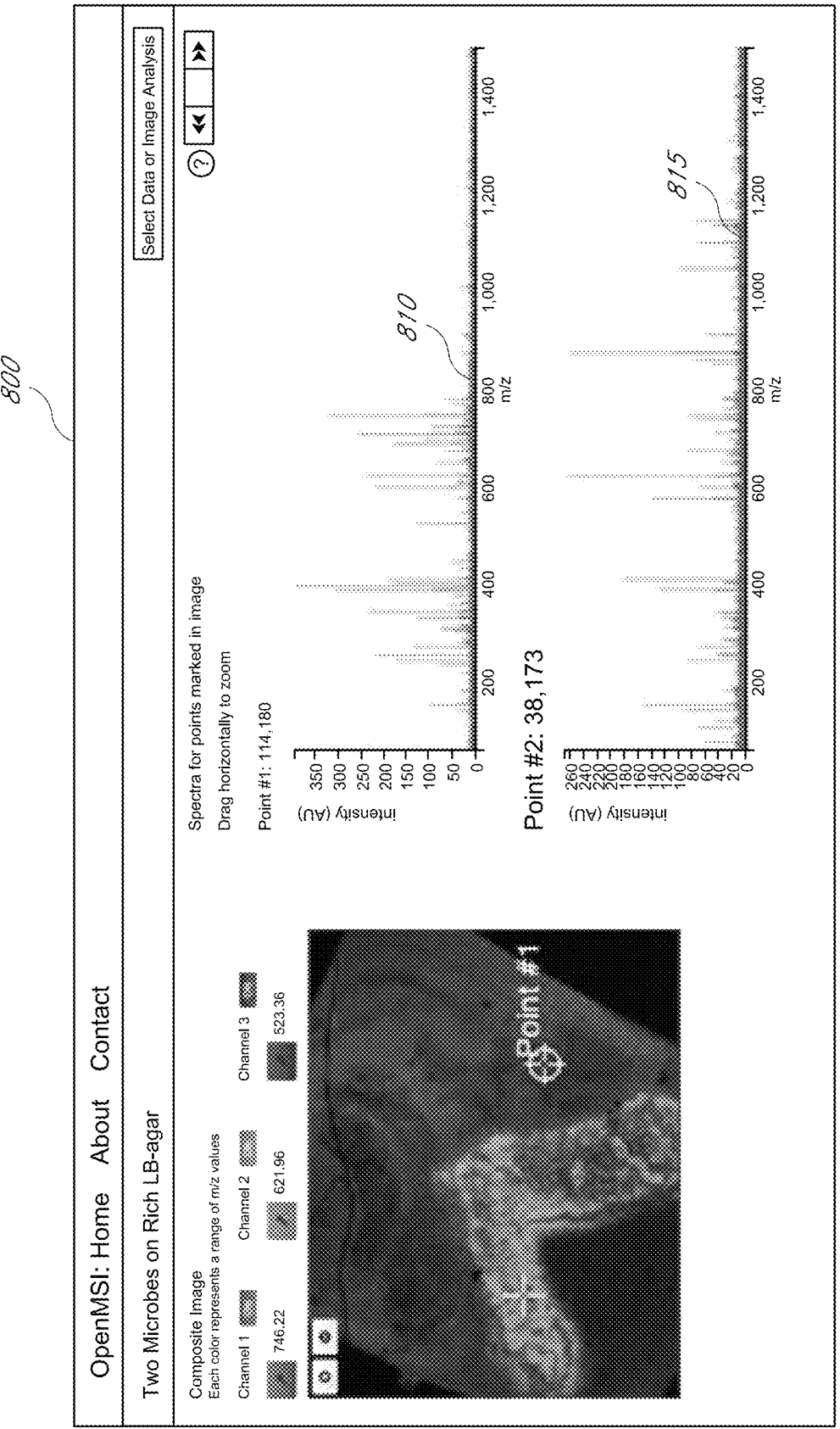
FIG. 8 illustrates an example OpenMSI web-based viewer application showing the ion-image viewer on the left and the spectrum plots for two selected locations (marked by crosshair cursors) on the right.

FIG. 8 illustrates an example OpenMSI web-based viewer application embodiment showing the ion-image viewer on the left and the spectrum plots for two selected locations (marked by cross-hair cursors) on the right. In some embodiments, the viewer 800 may also be an application on a mobile device. Depending on the embodiment, the ion-image viewer 805 may retrieve a plurality of data chunks according to the disclosure, and delivers the ion-image to a user of the OpenMSI system efficiently. The two spectrum plots 810 and 815 show intensity on the Y axis and m/z values on the X axis. In some embodiments, the spectra plots 810 and 815 may be automatically updated and refreshed based on the respective points chosen by the user in the ion-image viewer 805. In some embodiments the spectrum plots may display other information (e.g., loadings from the dimension reduction) or be replaced by other matrix data visualizations.

Figure 9:
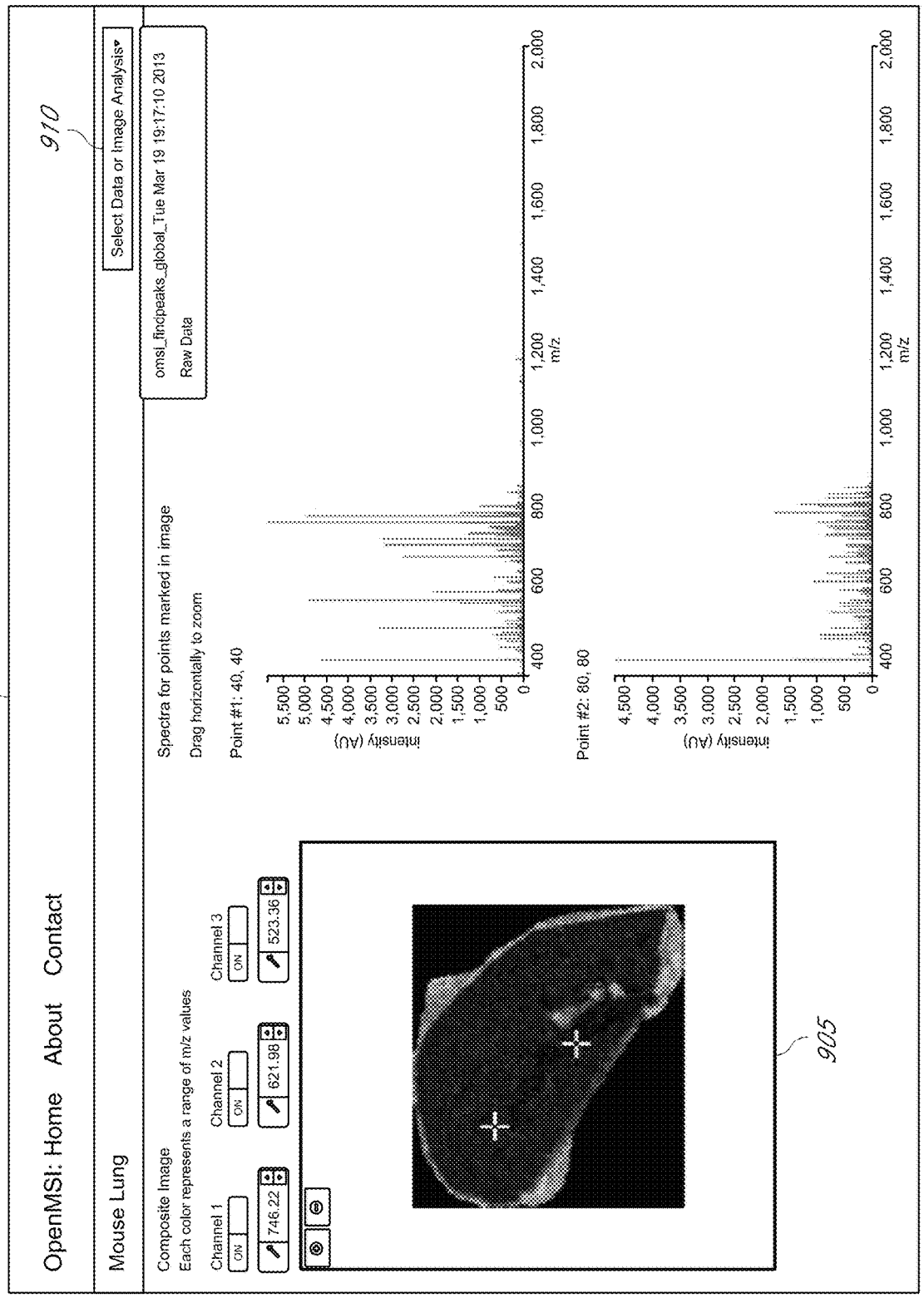
FIG. 9 illustrates an example OpenMSI web-based viewer application wherein raw spectroscopic data may also be displayed for users.

FIG. 9 illustrates an example embodiment of an OpenMSI web-based viewer application wherein raw data may also be displayed for users. In some embodiments, the viewer 900 may be an application on a mobile device. In some embodiments, the image viewer 905 may display metadata information related to the experiment, sample, and equipment, in addition to the retrieved image, which may be stored in a storage system according to this disclosure.

In some embodiments, the OpenMSI system may allow users to select specific data or image analysis. For example, the viewer 900 may include a link 910 for selecting data or image analysis in connection to the displayed image and spectra details. A user may then perform additional analysis on the selected and/or displayed dataset.

VI. Evaluation and Results

A. Data Layout Optimization and Performance

The effectiveness of the various data layout optimizations available as part of the OpenMSI system's file format and APIs are evaluated. Although, ASCII/text based formats based, e.g., on XML, are very common in MSI, such formats are not optimized for efficient data storage and fast data access but rather focus on ease of use of the format. Therefore, the various optimized data layouts are compared to the common and much more efficient continuous binary data layout. However, it is worth noting that due to the large storage and data read overheads that text-based formats exhibit, the improvements in performance for data read and storage requirements would be in practice one or several orders of magnitude greater, if text-based formats were also taken into account.

Identifying a Suitable Hybrid Chunked Data Layout.

In some embodiments, a spectra-aligned chunking may be able to provide optimal performance for access of single, complete spectra while providing poor performance for to access of ion-images and vice versa for image-aligned chunked data (see data layout as disclosed herein). In some instances, hybrid chunked data layouts promise to provide fast read performance to arbitrary subcubes of the data while providing a compromise in performance for access to ion-images and spectra. However, the large differences in resolution in physical space (x,y) and the spectra (m/z) makes finding a well-performing hybrid chunking challenging. To identify a good hybrid chunked data layout a large-scale auto-tuning type experiment is performed to explore: i, iii) the read performance of spectra, ion images, and subcubes; iv) the data write performance; and v) the storage requirements of all k×k×l hybrid chunked data layouts with $l \in [128, 256, 512, 1024, 2048, 4096, 8192]$ and $k \in [1, 2, 4, 8, 16, 32]$ using a 100×100×100,000 sized dataset as reference. These experiments have shown that a chunked layout of 4×4×2048 may provide good performance for access of both ion-images and spectra. More details about these experiments are discussed with regard to Evaluation of Hybrid Chunked Data Layouts and FIGS. 12-16. Based on the results from these experiments as discussed, a hybrid chunking of 4×4×2048 was chosen to exemplify the performance characteristics of a hybrid chunked data layout.

Figure 5:
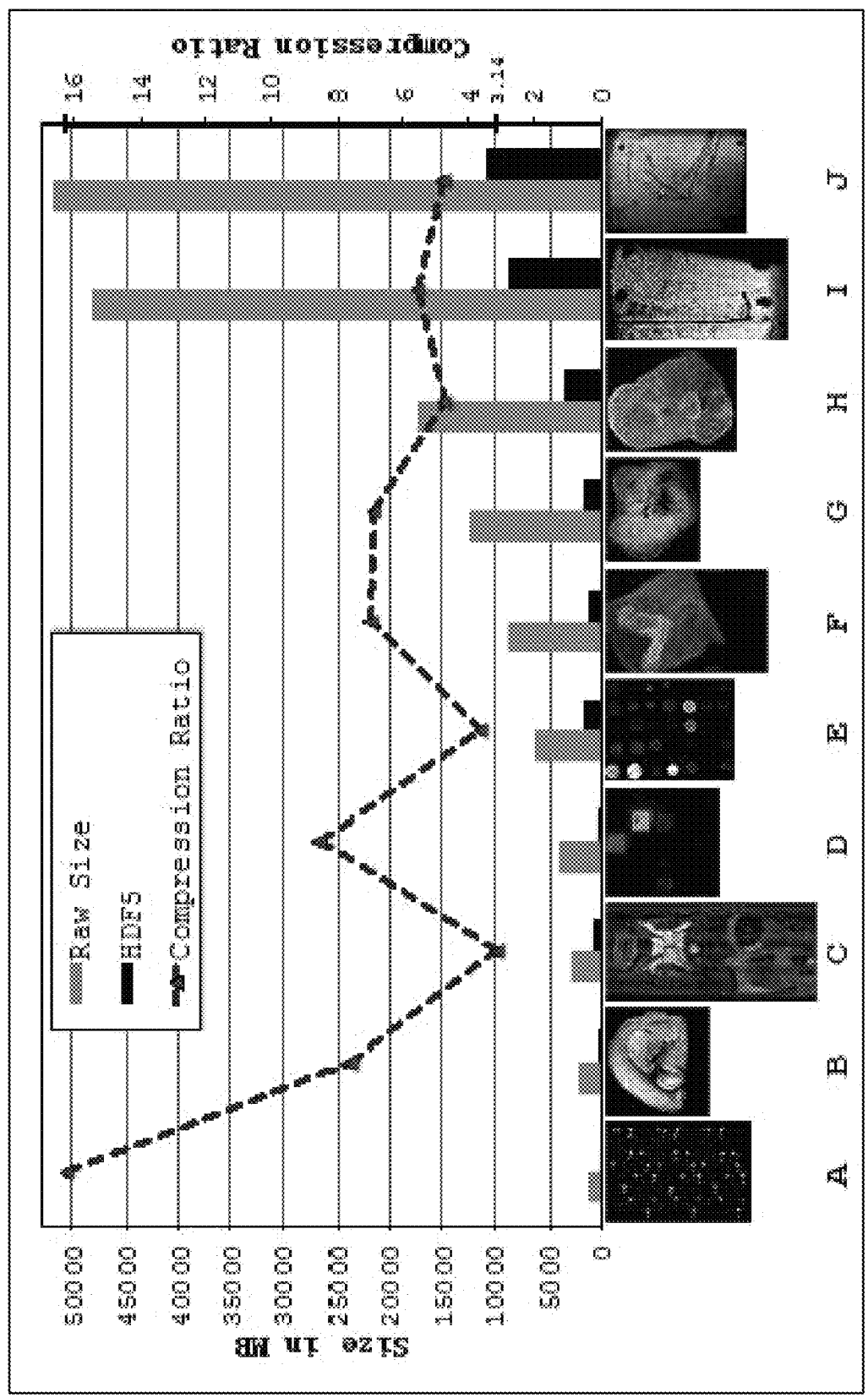
FIG. 5 is a diagram illustrating the size difference between original data and the OpenMSI HDF5 data.

Data Compression. Next the ability of data compression to reduce file size was examined FIG. 5 shows a comparison of the size of a diverse set of MSI dataset (and/or other types of neurosensory and/or spectroscopic dataset) stored using the OpenMSI HDF5-based format compared to the standard raw binary data. Three to sixteen times compression without loss of data was observed. As illustrated in FIG. 5, size of the original image data (shown as gray bars) are compared to the same data stored using the OpenMSI HDF 5 data format and storage system components (black bars), using Gzip compression and a hybrid chunking of 4×4×2048. For example a 3 GB image could be compressed to only 0.5 G using the OpenMSI system's file format. This means, even when storing the raw MSI data twice to accelerate data access, the resulting omsi HDF5-based files are still much smaller than the raw binary data. The combination of chunking and compression has also shown to be a viable solution for efficient storage of partial MSI data cubes and processed spectra. In this case the data may still described as a complete MSI data cube. However, chunks are allocated by HDF5 during the first write—i.e., empty data chunks are never allocated by HDF5—while missing data values are automatically completed with zero values upon read. Furthermore, partial chunks are completed with 0's which can be compressed very efficiently with very little overhead. To illustrate the effectiveness of this approach, an example of a MSI dataset of a lung with a resolution of 132×149×300,000 was chosen. In the example dataset, an arbitrary region of interest consisting of 12,654 spectra has been imaged and the spectra were pre-processed to remove background noise. From the total 5,900,400,000 data values (i.e., ~11,800 MB) only 107,007,401 values (i.e., ~214 MB) are non-zero. Using a hybrid chunked layout of 4×4×2048 in combination with compression, the OpenMSI system requires only ~196 MB to store the complete 132×149×300,000 data cube while allowing the user to seamlessly interact with the data as if it were a complete MSI data cube.

Optimizing Data Read Performance.

Figure 6A:
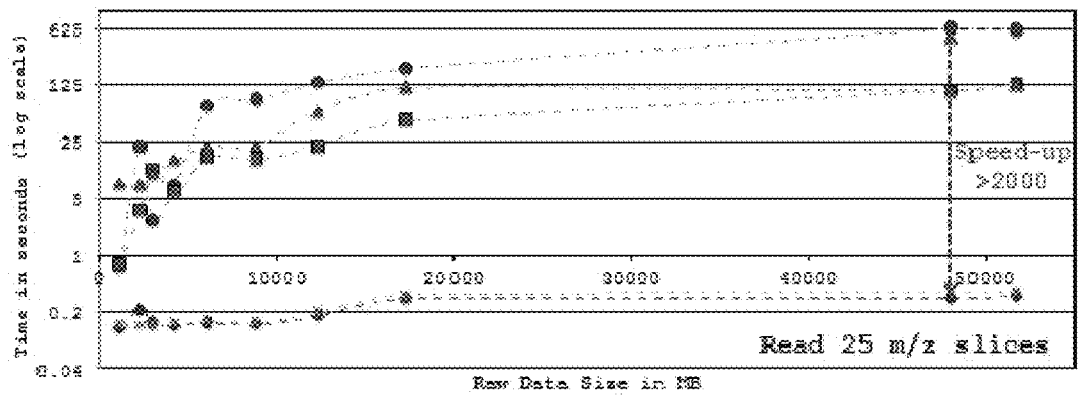
FIG. 6A illustrates serial read performances of a common data access pattern in which 25 m/z slices are read.
Figure 6B:
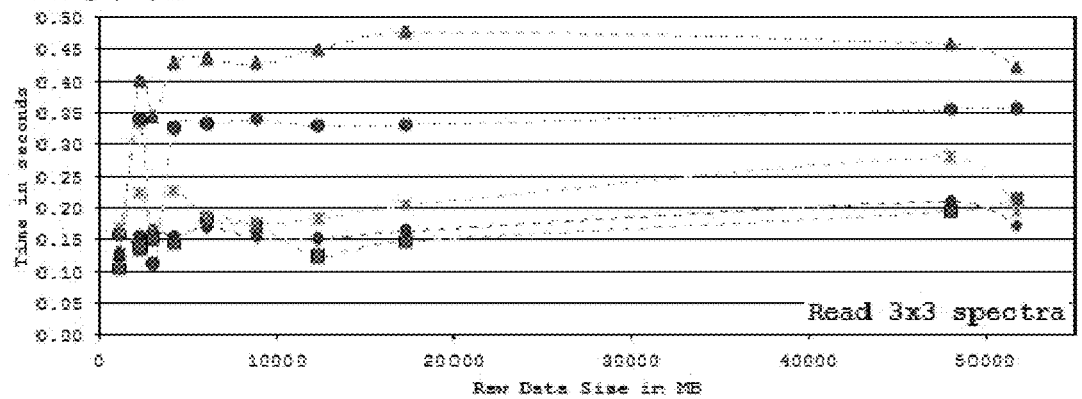
FIG. 6B illustrates serial read performances of a common data access pattern in which 3×3 spectra are read.
Figure 6C:
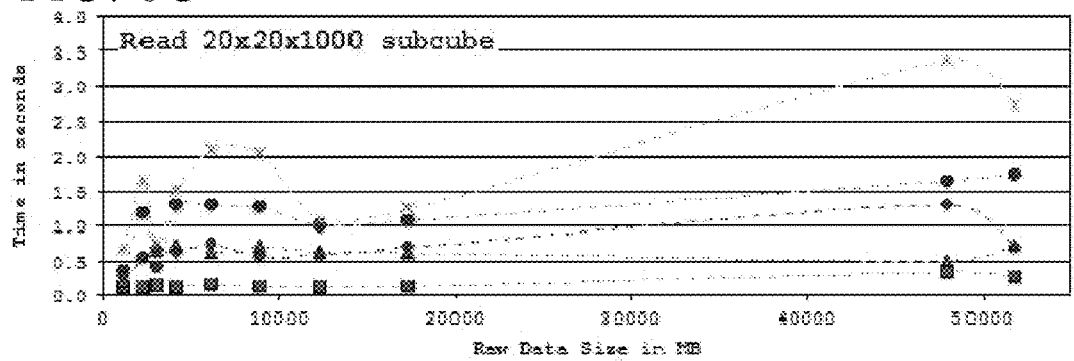
FIG. 6C illustrates serial read performances of a common data access pattern in which 20×20×1000 sub-cubes are read.

A set of performance tests have been performed to evaluate the performance of the OpenMSI system's file format and to identify suitable data layouts. To evaluate performance of different data layouts for the common selective read patterns, the following three representative test cases are set up:

i) Read 25 consecutive m/z slices (as shown in FIG. 6A)

ii) Read a 3×3 subset of complete spectra (as shown in FIG. 6B)

iii) Read a 20×20×1000 sub-cube of the data (as shown in FIG. 6C)

The performance of the following five data layouts were compared:
  i) The default monolithic layout (baseline),
  ii) A hybrid (4×4×2048) chunking with compression (gzip)
  iii) A hybrid (4×4×2048) chunking without compression (gzip),
  iv) An auto chunked data layout with compression (gzip), and
  v) The same auto chunked layout without compression.

The auto-chunked data layout may use data replication in addition to chunking and compression to further optimize data read performance Here, for example, the data is stored twice using a spectrum-aligned and an image-aligned data chunking strategy (see FIGS. 6A-6C), while the OpenMSI file API automatically chooses the best-suited data layout for a given data read.

Figure 6D:
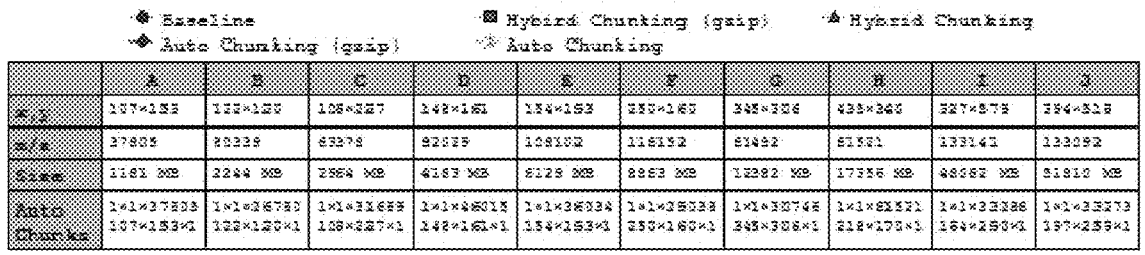
FIG. 6D illustrates details regarding each test dataset, including spatial (x,y) and spectra (m/z) resolutions, size, and size of the auto chunks.

To demonstrate the performance across a broad range of MSI datasets, ten MSI datasets (named A, B, C, D, E, F, G, H, I, and J as shown in FIG. 6D) were chosen to show varying spatial and m/z resolution and range in size between 1 GB up to 50 GB (see, FIG. 6D for the spatial resolution (x,y), spectra m/z value, size, and auto chunk size of each dataset) All tests were performed on a local desktop workstation equipped with two quad-core Intel Xeon E5630 running at 2.53 GHz CPUs and 20 GB of RAM. All data was stored on a local 1 TB regular spinning-disk hard drive. The tests were performed in serial, i.e., only one of the available compute cores was used in the tests. The tests were implemented in Python, and a sample implementation of the test is included in appendix 1. Fifty random read operations were performed for each of the 150 test cases, while the following was randomized i) the spectra m/z value for the image read; ii) the spatial (x/y) location for spectra read; iii) and (x,y, m/z) origin for the sub-cube read. The $95^{th}$ percentile of all measurements are reported to demonstrate the expected read performance for the different data layouts.

FIGS. 6A-6C summarize the results from all selective read performance tests, including image reads, spectra reads, and sub-cube reads. FIG. 6A illustrates serial read performances of a common data access pattern in which 25 m/z slices are read. FIG. 6B illustrates serial read performances of a common data access pattern in which 3×3 spectra are read. FIG. 6C illustrates serial read performances of a common data access pattern in which 20×20×1000 sub-cubes are read. In the example of FIG. 6A, the baseline data layout shows particularly poor performance for the read of ion-images, requiring more than 600 seconds to retrieve just 25 consecutive images for dataset I. Even though 25 ion images constitute only ~9.5 MB of binary data, the entire ~48 GB data volume needs to be traversed to retrieve the data using the baseline layout. For the hybrid-chunked data layout (with compression) speed-ups of up to ~6.3 for the image read in FIG. 6A, ~2.6 for the spectrum read in FIG. 6B, and ~11.2 for the sub-cube read in FIG. 6C compared to the baseline data layout were observed. While this improvement in performance is significant, the read performance of the hybrid-chunked data layout might still be insufficient for many time-critical analysis tasks and interactive data applications. This could be due to the compromise the hybrid chunking is making in terms of performance to support orthogonal data access patterns.

For the auto-chunked data layout (with compression), speed-ups of more than 2000 were observed for the image read enabling data read of ion-images and spectra in less than 0.3 seconds even for the largest test datasets. It was also observed that the performance for reading ion-images using the auto-chunked approach depends mainly on the spatial resolution of the images and is mostly independent of the resolution of the data in m/z (i.e., the total number of images) Similarly it was observed that the read of spectra is largely independent of the spatial resolution of the data in the auto-chunked case. These results suggest that this approach is scalable to meet the needs of data at scales higher than what is typically generated today. Using this approach enabled fast retrieval of both spectra and ion-image directly from file without requiring caching of the data in memory. The performance observed is sufficient to support interactive data exploration tasks even for very large MSI datasets and/or other types of large data sets, such as neurosensory datasets, spectroscopic datasets, and so forth.

When comparing the performance of the data layouts with and without using compression, it was observed that the compressed data layouts performed significantly better even for reads from local disk. In cases where the data is stored on external storage systems, this behavior may be expected to be further amplified due to the reduced amount of data that needs to be transferred via the network when the data is compressed.

Performance of Web-Based Data Access Operations.

Figures 7A, 7B, 7C:
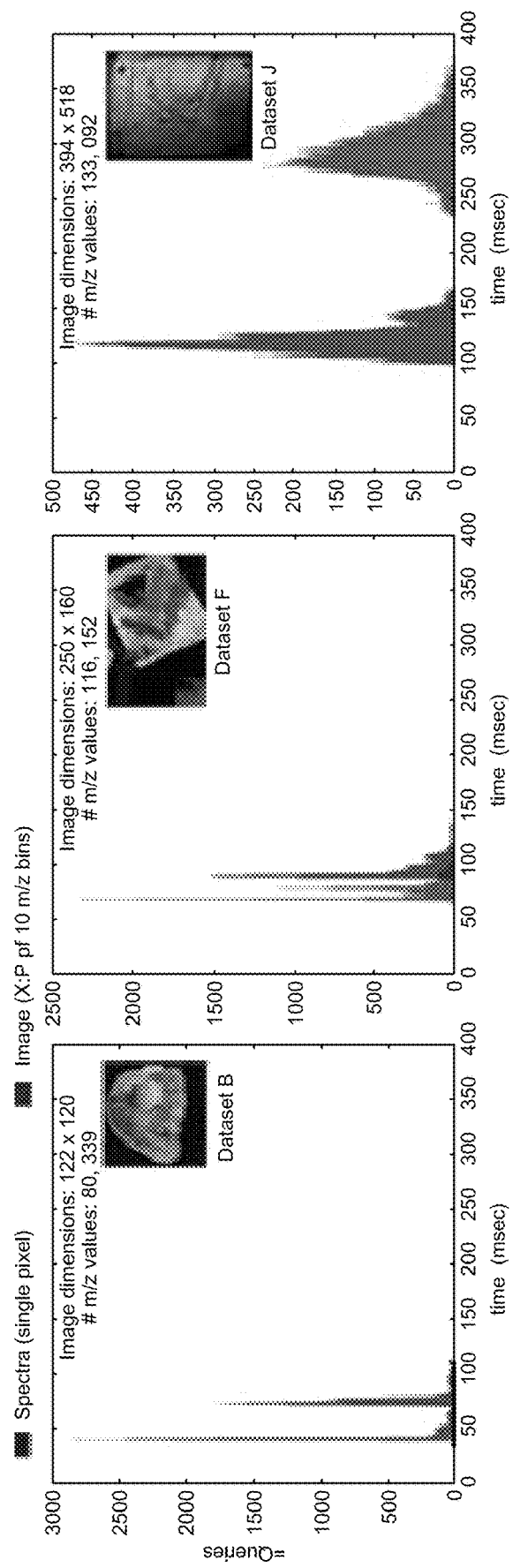
FIG. 7A is a diagram illustrating web-based read performances for a test dataset with image dimensions of 122×120.
FIG. 7B is a diagram illustrating web-based read performances for image dimensions of 250×160.
FIG. 7C is a diagram illustrating web-based read performances for image dimensions of 394×518.

To test the performance of the platform's ability to access data across the Internet, images and spectra were programmatically retrieved from the server to a laptop computer using a standard 1 Gigabit-Ethernet connection. FIGS. 7A-7C are diagrams illustrating web-based read performances according to some embodiments of the OpenMSI system. These figures show the histogram of the 20,000 random single spectrum and 20,000 random ion-image data requests returning a maximum intensity projection over 10 m/z bins for each of the test cases. Very reliable read performances were observed in all cases, indicated by the compact distribution of response times in the histograms Specifically, FIG. 7A is a diagram illustrating web-based read performances for image dimensions of 122×120. FIG. 7B is a diagram illustrating web-based read performances for image dimensions of 250×160. FIG. 7C is a diagram illustrating web-based read performances for image dimensions of 394×518. With the expectation that the size of a particular MSI file (and/or other types of neurosensory data file, spectroscopic data file, and so forth) would significantly affect the time required to transfer results, the largest dataset J (as shown in FIG. 7C) with a resolution of (394×518) pixels and 133,092 m/z bins, the medium size dataset F (as shown in FIG. 7B) with a resolution of (250×160) pixels and 116,152 m/z, and the relatively small dataset B (as shown in FIG. 7A) with a resolution of (122×120) pixels and 80,339 m/z bins were chosen. For each file, twenty-thousand images and twenty-thousand spectra were retrieved from the server at random spatial coordinates or m/z ranges, respectively. These requests were implemented programmatically in Matlab® and a sample implementation of the test is available in Appendix II. In other embodiments, other languages may be used to implement the requests. The computer requesting the data was a MacBook Pro laptop with a 2.2 GHz Intel Core i7 processor and 8 GB of 1333 MHz RAM. Other types of computing equipment may be used to request such data. All of the files were stored on the physical, regular spinning disk of that server. The laptop was connected to a standard (1 GBit) office Ethernet connection in Berkeley, Calif. With the specified parameters of the API described above, the qslice and qspectrum commands were used for these tests and exercised in Matlab® using the urlread command. For both tests, data was returned as a JSON structure as text.

The tests show that the OpenMSI system reliably supports sub-second data retrieval times for a wide range of MSI file sizes. For the MSI dataset of the brain (dataset B, as shown in FIG. 7A), the average time to retrieve a spectrum was 74 msec and the average time to retrieve an image was 43 msec. For the biofilm imaging dataset (dataset F, as shown in FIG. 7B), the average time to retrieve a spectrum was 97 msec and the average time to retrieve an image was 78 msec. Lastly, for the large image of roots and soil (dataset J, as shown in FIG. 7C), the average time to retrieve a spectrum was 126 msec and the average time to retrieve an image was 294 msec. These results are consistent with the performance observed in the previous section for read performance directly from file.

URL-based data analysis sharing is also enabled in the OpenMSI system. Using the OpenMSI web viewer prototype, a URL can be shared that presents the user with an interactive view based on specified visualization parameters. An example view of the OpenMSI web viewer prototype is shown in FIG. 8.

VII. Details of Data Processing and Retrieval

Figure 17:
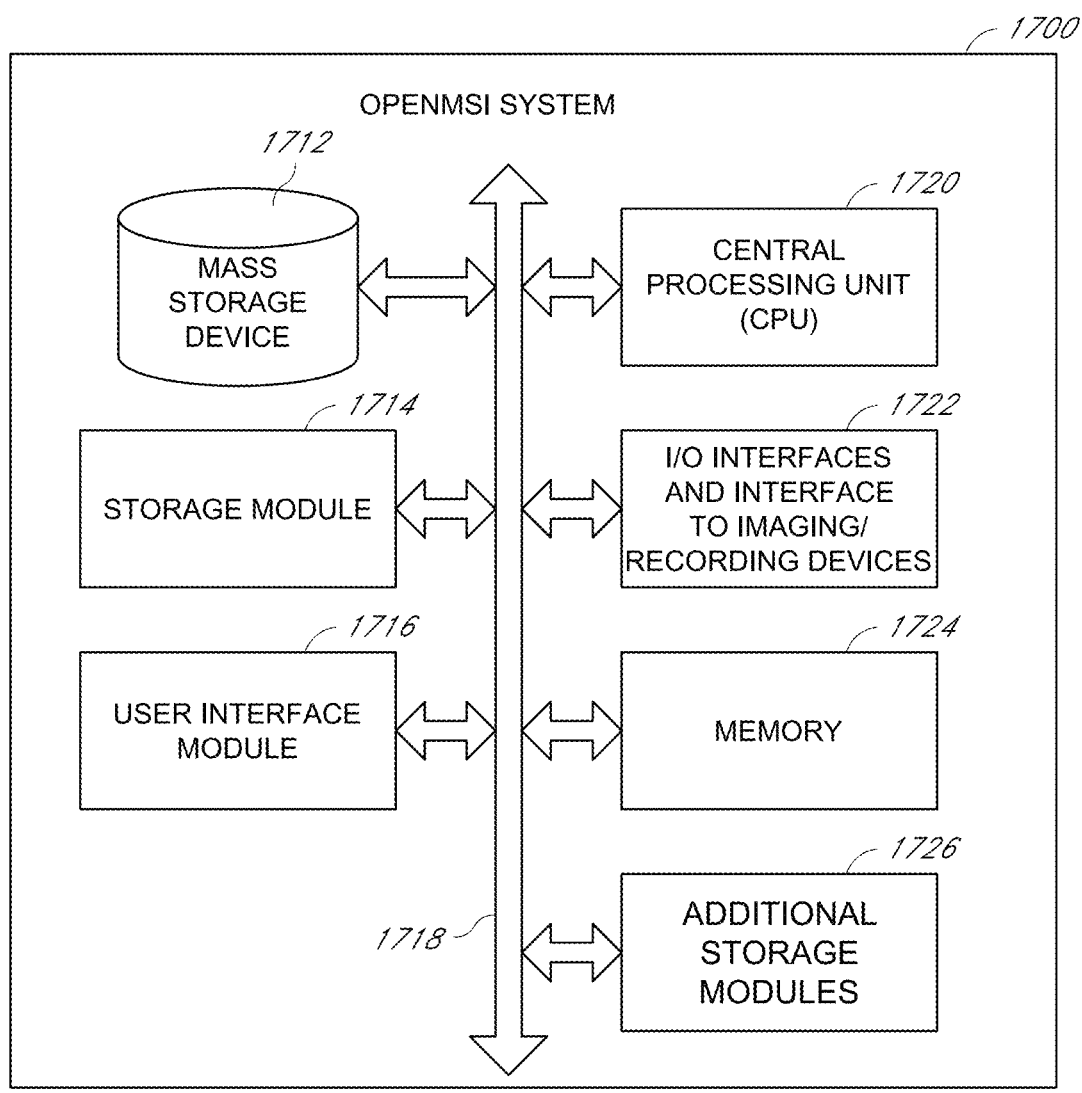
FIG. 17 is a block diagram that illustrates an example embodiment of an OpenMSI system with various system components and modules.

FIG. 17 illustrates an example embodiment of an OpenMSI system 1700. The OpenMSI system 1700 may include, depending on embodiment, I/O interfaces and interfaces to one or more imaging/recording devices 1722 (such as MSI imaging devices), the interfaces may receive neurosensory and/or spectroscopic data and associated metadata from the imaging instruments and other external data sources. The OpenMSI system 1700 may include, depending on the embodiment, a mass storage device 1712, which may be used to store MSI data and/or other types of large data, such as neurosensory data, spectroscopic data, and so forth. The OpenMSI system may further include a storage module 1714, which may store structured MSI data using a file format such as HDF5, for purposes of efficient retrieval and access using the system/methods described herein. In some embodiments, the storage module is configured to store the neurosensory data, spectroscopic data, and so forth, and metadata in one or more spectrally aligned data chunks, image aligned data chunks, and/or hybrid data chunks. The user interface module 1716 may also be included in the OpenMSI system, which enables users of the system to efficiently access neurosensory and/or spectroscopic data using Web API and URL patterns, for example. The user interface module 1716 may be configured to retrieve ion image slices, m/z spectra data, or arbitrary sub-cubes from the stored data chunks. The user interface module 1716 may also be configured to graphically display the accessed neurosensory and/or spectroscopic data, derived analysis data, and relevant metadata to the user. The OpenMSI system 1700 may also include CPU 1720 and memory 1724. Depending on the embodiment, additional storage modules 1726 may be used to store neurosensory and/or spectroscopic data, such as replicated copies of the same data and/or metadata.

Figure 18:
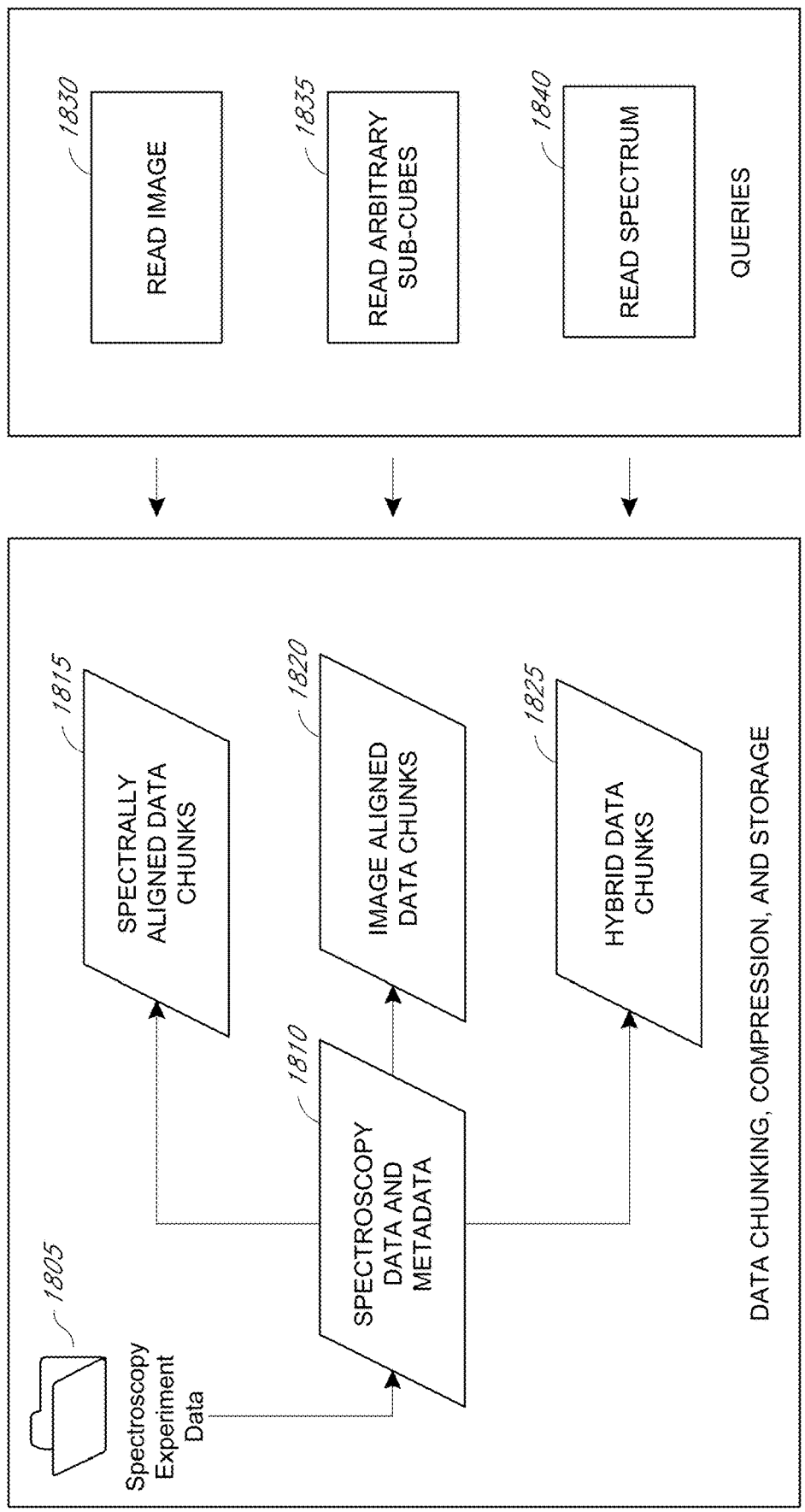
FIG. 18 is a block diagram illustrating one example of a data chunking, storage and retrieval system according to some embodiment of the OpenMSI system.

FIG. 18 illustrates an example data chunking, storage and retrieval system according to some embodiment of the OpenMSI system 1700. Spectroscopy experiment data 1805 (mass spectrometry imaging data or alternatively, other types of large-scale data, such as neurosensory data, spectroscopic data, and so forth, and spectra generated by absorption, emission, energy, frequency, reflectance, resonance, molecular vibration, and/or secondary emission, etc.) may be received by the OpenMSI system 1700. The received spectroscopy experiment data 1805 may be processed into spectroscopy data and metadata 1810. The processed data 1810 may then be chunked and stored as spectrally aligned data chunks 1815, image aligned data chunks 1820, and hybrid data chunks 1825, depending on the specific dataset and embodiment.

Depending on the embodiment, queries for retrieving and accessing the stored data may be sent, and the queries could be formatted to send requests to read image 1830, read arbitrary sub-cubes 1835, or to read spectrum 1840.

a. Data Read

Figure 10:
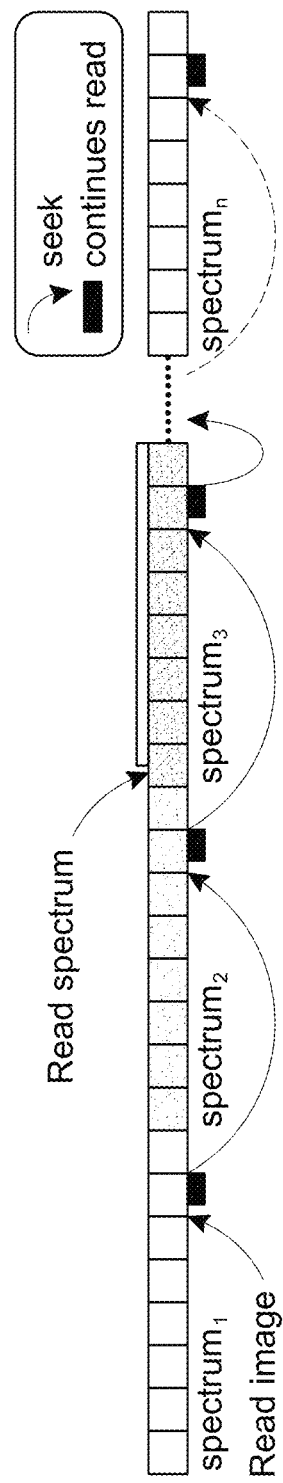
FIG. 10 illustrates a layout commonly used for storing spectroscopic data (such as MSI data) in binary form.

FIG. 10 illustrates an embodiment of a layout commonly used for storing MSI data and/or other types of data such as neurosensory data, spectroscopic data, and so forth, in binary form. The data is stored as a single monolithic block arranged on disk one spectrum at a time. This layout is well suited for retrieval of single full spectra from disk (red) but requires a large number of seek and small read operations to retrieve a single ion-image (blue). In order to retrieve an ion image, the full dataset has to be traversed, leading to poor performance in particular for large MSI datasets.

b. Data Layout

Figure 11:
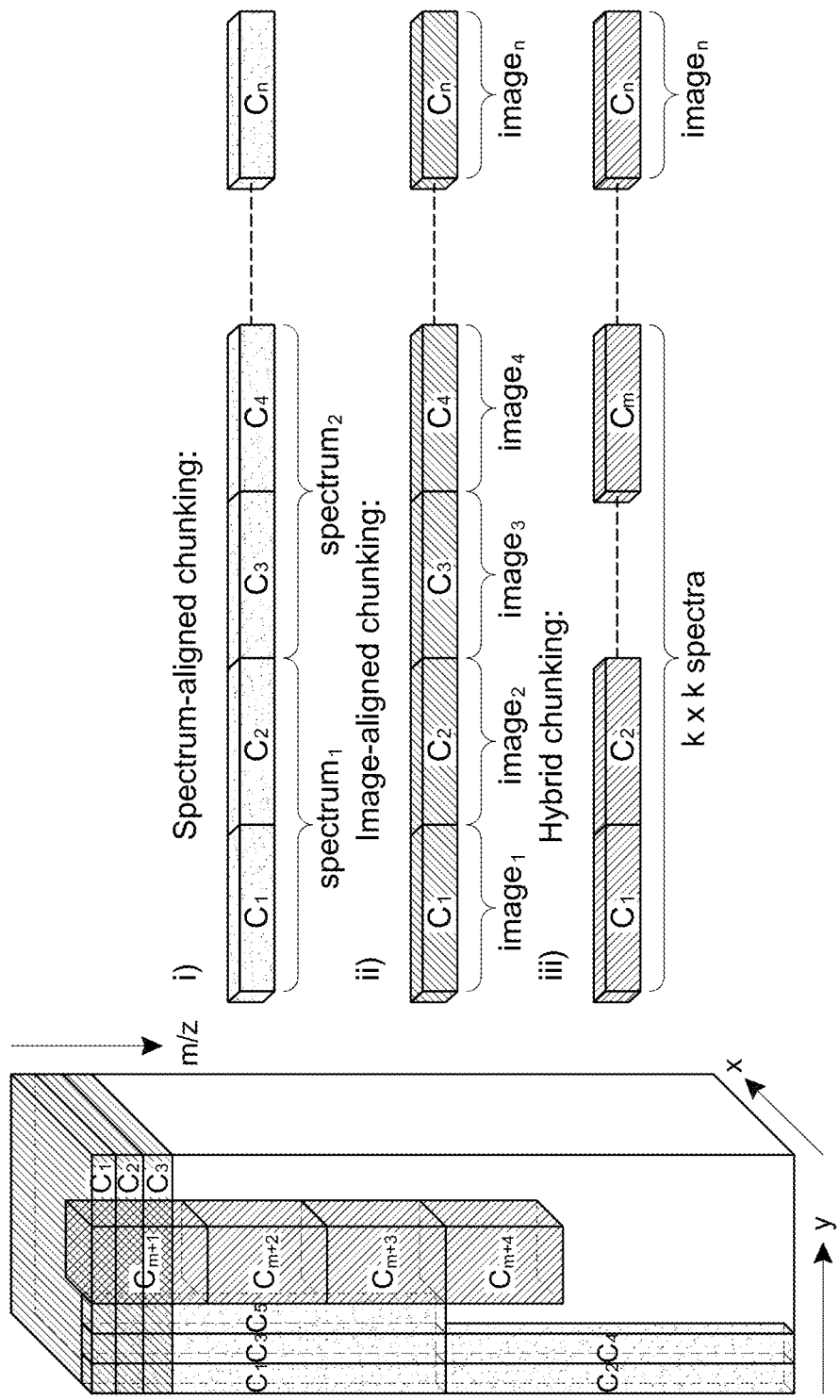
FIG. 11 illustrates different basic chunked data layouts for storage of spectroscopic data (e.g., MSI data).

FIG. 11 illustrates different basic chunked data layouts embodiment for storage of MSI and/or other types of large scale data such as neurosensory data, spectroscopic data, and so forth. Spectrum-aligned chunking, image-aligned chunking, and hybrid chunking are shown. Use of chunking enables independent read/write access to individual data chunks (e.g., sub-blocks of neurosensory and/or spectroscopic data) and can significantly improve the locality of data as it is linearized on disk. Chunking allows in this way optimization of the data layout to improve the performance of a select set of I/O patterns.

c. Description of the OpenMSI WebAPI URL Patterns

The basic URL patterns are constructed as follows: <baseURL>/<command>/?<querystring> and consist of the following three main components:

<baseURL>: The basic URL where the server is running, e.g. https://openmsi.nersc.gov/openmsi/

<command>: Depending on which data/action requested, a different command may be used. The main available commands are:

qmetadata: Request metadata information.

qmz: Request information about the m/z axis of the data.

qslice: Request ion-slices (raw or derived) from the data.

qspectrum: Request spectra (raw or derived) from the data.

qcube: Request arbitrary structured subsets of the data.

(client: Request client webpages e.g, the OpenMSI viewer.)

<querystring>: List of different function parameters.

In the following, the different URL patterns and the syntax for specifying data selections are described:

qmz: Requesting m/z Data

Request information about the static m/z axes. This function is provided to avoid repeated transfer of the usually static m/z axes information. In most cases the m/z axes data is requested once at the beginning and reused afterwards. In cases where the m/z axes for spectra is not static—e.g., in the case of processed spectra—the qslice pattern returns the intensity values as well as the corresponding m/z values for the spectra, otherwise the m/z values are omitted.

Base Pattern:

https://openmsi.nersc.gov/openmsi/qmz/?<querystring>

Query String Parameters:

Required query string parameters:

file: The filename/path of the OpenMSI HDF5 datafile to be used.

expIndex: The index of the experiment stored in the file.
Required query parameters when requesting from raw MSI data:
    dataIndex: The index of the MSI dataset to be used.
Required query parameters when requesting from analysis data:
    anaIndex: The index of the analysis dataset to be used. Note, anaIndex and anaIdentifier are redundant and only one should be specified.
    anaIdentifier: Identifier string of the analysis dataset. Note, andIndex and anaIdentifier are redundant and only one should be specified.
    qslice_viewerOption: Integer indicating which qslice viewerOption should be used. Some analysis may support multiple different viewer behaviors for the qslice URL pattern. This optional parameter is used to indicate which viewer behavior should be used.
    qspectrum_viewerOption: Integer indicating which qspectrum viewerOption should be used. Some analysis may support multiple different viewer behaviors for the qspectrum URL pattern. This optional parameter is used to indicate which viewer behavior should be used.
Returns:
    Returns error message or JSON object with the following entries:
    values_spectra: Axes values for the spectra or null if missing in the data.
    label_spectra: Axes label to be used for the spectrum axes.
    values_slice: Values for the z axis to be used for identifying image slices or null if missing in the data. This return value is optional and is only present if different from values_spectra.
    label_slice: Label for the z axis to be used for image slices. This return value is optional and is only present if different from label_spectra.
qmetadata: Requesting Metadata Information
Request JSON object with metadata information pertaining to the list of available files, a file, an experiment, an analysis, an instrument or a sample.
Base Pattern:
https://openmsi.nersc.gov/openmsi/qmetadata/?<querystring>
Query String Parameters:
    Required query arguments:
    mtype: Type of metadata requested, one of:
        filelist,
        file,
        experiment,
        experimentFull,
        analysis,
        instrument,
        sample,
        dataset.
Additional required query arguments for mtype experiment, experimentFull, instrument, and sample:
    filename: The filename/path of the OpenMSI HDF5 datafile.
    expIndex: The index of the experiment stored in the file.
Additional required query arguments if mtype is analysis:
    filename: The filename/path of the OpenMSI HDF5 datafile.
    expIndex: The index of the experiment stored in the file.
    anaIndex: The index of the analysis dataset to be used (default None). Either andIndex or anaIdentifier may be provided.
    anaIdentifier: Identifier string of the analysis dataset (default None). Either andIndex or anaIdentifier may be provided.
Additional required query arguments if mtype is dataset:
    filename: The filename/path of the OpenMSI HDF5 datafile.
    expIndex: The index of the experiment stored in the file
    Raw MSI data indicator (only when requesting information for a raw MSI dataset):
        dataIndex: Index of the MSI dataset
    Analysis data indicators (only needed when requesting information for a derived analysis dataset):
        anaIndex: The index of the analysis dataset to be used (default None). Either anaIndex or anaIdentifier may be provided.
        anaIdentifier: Identifier string of the analysis dataset (default None). Either anaIndex or anaIdentifier may be provided.
        anaDataName: Name of the analysis dataset for which metadata information is requested
Returns:
    The function returns a JSON object with a dictionary describing the requested metadata information in a structured fashion.
qspectrum: Requesting Spectra
Request JSON object or PNG image plot of: i) a single spectrum, ii) multiple spectra or iii) the difference of two or multiple spectra.
Base Pattern:
    https://openmsi.nersc.gov/openmsi/qspectrum/?<querystring>
Query String Parameters:
    Required query arguments:
        filename: The filename/path of the OpenMSI HDF5 datafile.
        expIndex: The index of the experiment stored in the file.
        format: Output format of the returned data, one of: JSON or PNG
        x:x-index(s) of the pixel/spectrum to be loaded. See Section Data Selection below.
        y:x-index(s) of the pixel/spectrum to be loaded. See Section Data Selection below.
    Required query arguments when requesting from raw MSI data:
        dataIndex: Index of the MSI dataset
    Required query arguments when requesting spectra for derived analyses:
        anaIndex: The index of the analysis dataset to be used (default None). Either anaIndex or anaIdentifier may be provided.
        anaIdentifier: Identifier string of the analysis dataset (default None). Either anaIndex or anaIdentifier may be provided.
        anaDataName: Name of the analysis dataset from which the spectra should be loaded (default None). If no anaDataName is provided then the function will try and figure out which dataset to be used based on what the analysis developer has specified in the implementation of the qspectrum pattern in the corresponding derived analysis class of omsi_analysis_base. In this case the behavior depends directly on which viewerOption is used.

viewerOption: Integer indicating which default behavior should be used for the given analysis (Default=0). Using this parameter allows the analysis developer to provide multiple different display options for an analysis and to expose spectra from data dependencies.

Additional optional query parameters:
findPeaks: Execute peak finding for the retrieved spectra (only used if format==BON). Valid values are 0 (False) and 1 (True).
reduction: String indicating the reduction operation to be executed on the first set of spectra defined by x, y. (Default is mean). Reduction operations are defined as strings indicating the numpy function to be used for data reduction. Valid reduction operations include e.g.: min, max, mean, median, std, var etc.

Optional query parameters when requesting difference spectra:
x2: x-index of the second pixel/spectra to be loaded. See Section Data Selection below.
y2: y-index of the second pixel/spectra to be loaded. See Section Data Selection below.
reduction2: String indicating the reduction operation to be executed for the second set of spectra selected by x2, y2 (default is None). Reduction operations are defined as strings indicating the numpy function to be used for data reduction. Valid reduction operations include e.g.: min, max, mean, median, std, var etc. Note if no reduction operation is applied, then the (x,y) shape of the first selection and second selection have to match in order to allow for the two arrays to be subtracted from each other.

Returns:
If format==JSON:
JSON object of the raw spectrum data (or multiple spectra if no reduction is applied), if only x, y (but not x2, y2) are specified and findPeaks is set to 0.
JSON object of the difference spectrum (or multiple difference spectra if no reduction is applied), if x,y and x2, y2 are specified findPeaks is set to 0.
JSON object of the raw spectrum (or difference spectra) data including additional fields with the results from the local peak finding (spectrum, peak_value, peak_pz) if findPeaks is set to 1.
In case that the m/z axis should be not static but change dynamically between spectra, then additional spectrum_mz key value with the m/z data is returned.
If format==PNG:
PNG plot of the raw spectrum data, if only x,y are specified or PNG plot of the difference spectrum data if x,y and x2, y2 are specified.

qslice: Requesting z Data Slices
Request JSON object (or gray-scale PNG image) of a single or multiple m/z image slices of the data.
Base Pattern:
https://openmsi.nersc.gov/openmsi/qslice/?<querystring>
Query String Parameters:
Required query arguments:
filename: The filename/path of the OpenMSI HDF5 datafile.
expIndex: The index of the experiment stored in the file.
format: Output format of the returned data, one of: JSON or PNG
z: z-index(s) of image slices to be loaded. See Section Data Selection below.

Required query arguments when requesting from raw MSI data:
dataIndex: Index of the MSI dataset
Required query arguments when requesting spectra for derived analyses:
anaIndex: The index of the analysis dataset to be used (default None). Either anaIndex or anaIdentifier may be provided.
anaIdentifier: Identifier string of the analysis dataset (default None). Either anaIndex or anaIdentifier may be provided.
anaDataName: Name of the analysis dataset from which the spectra should be loaded (default None). If no anaDataName is provided then the function will try and figure out which dataset to be used based on what the analysis developer has specified in the implementation of the qslice pattern in the corresponding derived analysis class of omsi_analysis_base. In this case the behavior depends directly on which viewerOption is used.
viewerOption: Integer indicating which default behavior should be used for the given analysis (Default=0). Using this parameter allows the analysis developer to provide multiple different display options for an analysis and to expose image slices from data dependencies.

Additional optional query parameters:
normalize: Binary value (O=False, 1=True) indicating whether the data retrieved should be normalized by dividing by the maximum value retrieved. (Relevant only if format==JSON).
reduction: String indicating the reduction operation to be executed for the selected image slices (axis=2). Reduction operations are defined as strings indicating the numpy function to be used for reduction. Valid reduction operations include e.g.: min, max, mean, median, std, var etc.

Returns:
JSON object or PNG image of the selected image slice(s).

qcube: Requesting Arbitrary Structured Subsets of the Data
Request JSON object of a general subset of the original MSI data or derived analysis data.
Base Pattern:
https://openmsi.nersc.gov/openmsi/qcube/?<querystring>
Query String Parameters:
Required query arguments:
filename: The filename/path of the OpenMSI HDF5 datafile.
expIndex: The index of the experiment stored in the file
Required query arguments when requesting from raw MSI data:
dataIndex: Index of the MSI dataset
Required query arguments when requesting spectra for derived analyses:
anaIndex: The index of the analysis dataset to be used (default None). Either anaIndex or anaIdentifier may be provided.
anaIdentifier: Identifier string of the analysis dataset (default None). Either anaIndex or anaIdentifier may be provided.
anaDataName: Name of the analysis dataset to be used.
Optional query arguments required for specification of data selections:
x: Selection string for x. Default value is ":" (i.e. all). See Section Data Selection below.
y: Selection string for y. Default value is ":" (i.e. all). See Section Data Selection below z: Selection string for z. Default value is ":" (i.e. all). See Section Data Selection below Additional optional query arguments:
  normalize: Normalize the data by dividing by the maximum retrieved data value.
  reduction: String specifying the first data reduction to be applied to the data. Reduction operations are defined as strings indicating the numpy function to be used for reduction. Valid reduction operations include e.g.: min, max, mean, median, std, var etc.
  axis: The data axis along which reduction should be applied (default value 2, i.e., the z axis).
  reduction2: Second reduction operation to be applied to the data.
  axis2: Axis along which the second reduction operation should be applied. Note that the dimensionality of the data is reduced by 1 by any prior data reduction operations (default value is 0).
  reduction3: Third reduction operation to be applied to the data.
  axis3: Axis along which the third reduction operation should be applied. Note that the dimensionality of the data is reduced by 1 by each prior data reduction operation (default value is 0).

Returns:
  JSON object defining the array of data retrieved.

d. Data Selection i. Basic Slicing

The data request URL's commonly support data selection parameters—e.g., x, y, or z—which are used to select the data that should be retrieved. There are several basic ways in which a user may specify data selections:

Range selection: "a:b" indicate that all values in the range of a and b should be selected. The upper bound b is not included in the selection, i.e., the selection 1:10 selects the elements 1,2,3,4,5,6,7,8,9.
  Index selection: "a" specifies a single index a that should be selected. NOTE: Specifying a single index usually implies that the dimensionality of the returned array is reduced by 1. E.g., a selection of [1,4,5] usually results in the retrieval of a single scalar corresponding to the item with index (1,4,5).
  All: ":" indicates that all values, i.e., the full range for the given dimension, should be selected.
  Index list: "[a,b,c,d]" indicates that the indices a,b,c,d should be selected.

ii. Multi-Dimensional Slicing

Several of the data URL patterns support multiple selection parameters, e.g., x and y in the case of qspectrum. These parameters are combined as [x,y,z] to allow retrieval of data from multi-dimensional arrays. The semantic for different combinations follows the same strategy as used by numpy (and h5py):

All-to-all: Most combinations of selections follow the all-to-all combination principal. That is all elements in the selection specified for x are combined with the selection specified for y. x=1:4 and y=1:3, hence, results in the retrieval of the elements [(1,1), (1,2), (2,1), (2,2) (3,1), (4,2)]. All-to-all selection, hence, always result in the retrieval of a single or multiple rectangular regions.
  Multiple index lists: In case that multiple index list selections are specified the lists are matched. This means if multiple lists are specified, then the lists may be of equal length and the lists are merged to define specific index-pairs to be selected. E.g, x=[1,2] and y=[4,5] results in the retrieval of the elements [(1,4), (2,4)] compared to an all-to-all matching, which would retrieve [(1,4), (1,5), (2,4), (2,5)]. This scheme allows for selection of arbitrary regions of interest. NOTE: When specifying multiple index lists, the dimensionality of the returned array may be reduced.

e. Evaluation of Hybrid Chunked Data Layouts

Goal: The goal of the evaluation has been to identify hybrid chunked data layouts that provide a compromise in performance for common data access patterns. The sustained performance for repeated selective data access operations were investigated.

Test Platform: All tests—were performed using a shared login node of the hopper.nersc.gov compute system equipped with 4 quad-core AMD 2.4 GHz Opteron 8378 processors (16 cores total) and 128 GB of memory using the Lustre-based scratch file system. All tests were performed in serial, i.e., only a single processor core was used.

Test Design:

To evaluate the performance of different data layouts, a set of test cases modeling the most common data access patterns in the analysis of MSI data (and/or other types of neurosensory data, spectroscopic data, and so forth) were designed. For each selection test case, the median time (indicating the sustained performance on an open file) and in select cases also the maximum time (indicating the selection performance after the first opening of the file) were reported. Each selection test case was repeated 50 times for each data layout using randomized selection parameters. All tests are performed using a 100×100×100,000 test dataset. The performance of k×k×l layouts with k=[1, 2, 4, 8, 16, 32] and l=[128, 256, 512, 1024, 2048, 4096, 8192] were evaluated. 32×32×128, 32×32×256, 32×32×512 were omitted due to the poor spectrum-at-a-time write performance of these data layouts.

Case 1: m/z Slice Selection: This test case models the selection of a series of m/z-slices of the data, and extracts a set of consecutive, full ion-images of the data.

○ Selection: [ : , : , $zmin:zmax$ ]
  ○ Randomized Selection Parameters: $zmin$
  ○ Dependent Selection Parameters: $zmax = zmin + 25$
  ○ Selection Size: $100 \times 100 \times 25 = 250,000$ records
  $= 500,000$ bytes
  $= 0.5 MB$ Case 2: Spectra Selection This test case models the selection of a 5×5 set of full spectra.

○ Selection: [$xmin: xmax, ymin: ymax$, :]
  ○ Randomized Selection Parameters: $xmin, ymin$
  ○ Dependent Selection Parameters: $xmax = xmin + 5, ymax = ymin + 5$
  ○ Selection Size: $5 \times 5 \times 100,000 = 200,000$ records
  $= 2,500,000$ bytes
  $= 5 MB$ Case 3: 3D Subcube Selection: This selection models the general access to consecutive sub-pieces of the data, e.g., when accessing data from a particular spatial region of the data related to a particular set of m/z data values.

○ Selection: [$xmin$: $xmax$, $ymin$: $ymax$, $zmin$: $zmax$]

○ Randomized Selection Parameters: $xmin$, $ymin$, $zmin$

○ Dependent Selection Parameters: $xmax = xmin + 5$, $$ymax = ymin + 5, zmax = zmin + 1000$$

○ Selection Size: $5 \times 5 \times 1,000 = 25,000$ records
  $= 50,000$ bytes
  $= 0.05 MB$ The amount of data that needs to be read and/or traversed on disk largely depends on the chosen data layout and may be significantly larger than the size of the selection. Moreover, the sustained performance, here measured by the median performance, is in practice often more important for analyses algorithms rather than web-applications, which require good worst-case performance, rather than good median performance. For hybrid chunked data layouts the general performance characteristics are in practice much more stable than for traditional monolithic data layouts (see, e.g., FIG. 12) so that the general trends of the median and 95%'il performance characteristics are often very similar.

Figure 12:
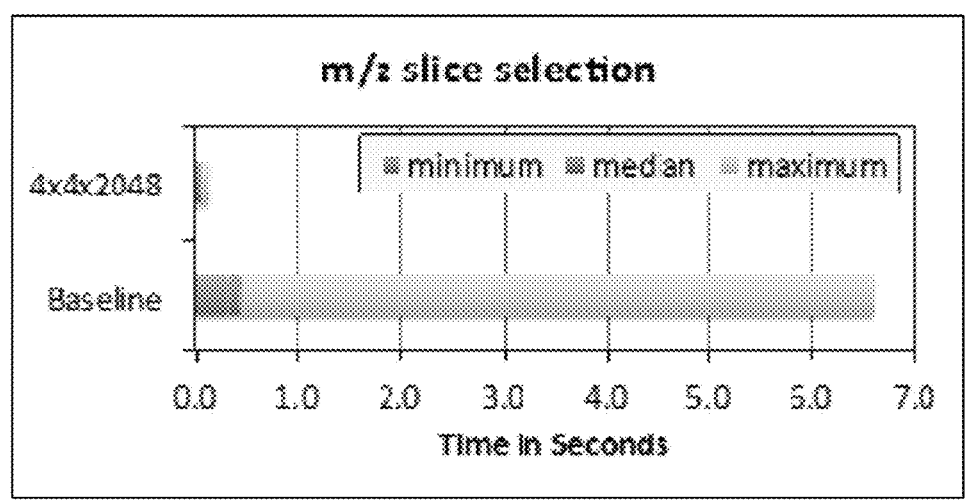
FIG. 12 shows the minimum, median, and maximum time for reading 25 consecutive ion-images from a 100×100×100,000 test dataset.
Figure 13:
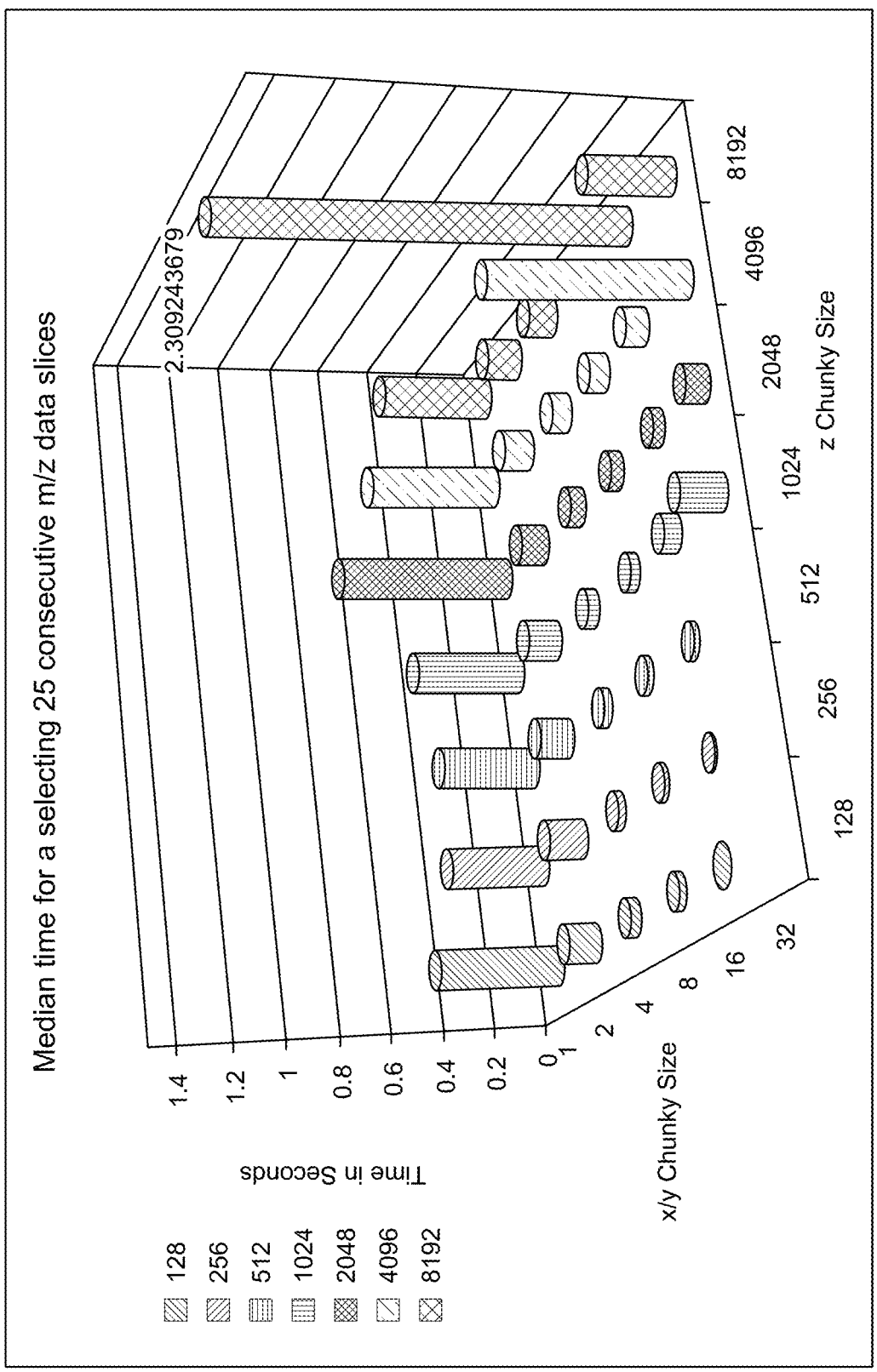
FIG. 13 illustrates, for the read of 25 ion-images, better read performance for hybrid chunked data layouts with larger spatial xy chunk sizes and smaller z chunk sizes is observed.

FIG. 12 shows the minimum, median, and maximum time for reading 25 consecutive ion-images from a 100×100×100,000 test dataset. The baseline, monolithic data layout requires traversal of the full dataset in order to retrieve ion images. In the baseline case, this behavior causes the full data to be cached in memory after just a few image read operations. This behavior leads to dramatic difference between the maximum and median read performance in the baseline case. Also, in cases where the size of the MSI data (and/or other types of neurosensory data, spectroscopic data, and so forth) exceeds the amount of available memory, the data can no longer be cached so that the median time approaches the maximum time. In contrast, the hybrid chunked data layout used in this example requires the read of typically only 625 independent chunks (i.e., 25*25 chunks in x and y) so that only a subvolume of 100×100×2048 is touched, avoiding traversal of the full data. This characteristic behavior leads to a much more stable read performance FIG. 13 illustrates, for the read of 25 ion-images, better read performance for hybrid chunked data layouts with larger spatial xy chunk sizes and smaller z chunk sizes was observed. This behavior is expected; smaller z chunk sizes imply that less data needs to be read while larger xy chunks imply that less chunks need to be read.

Figure 14:
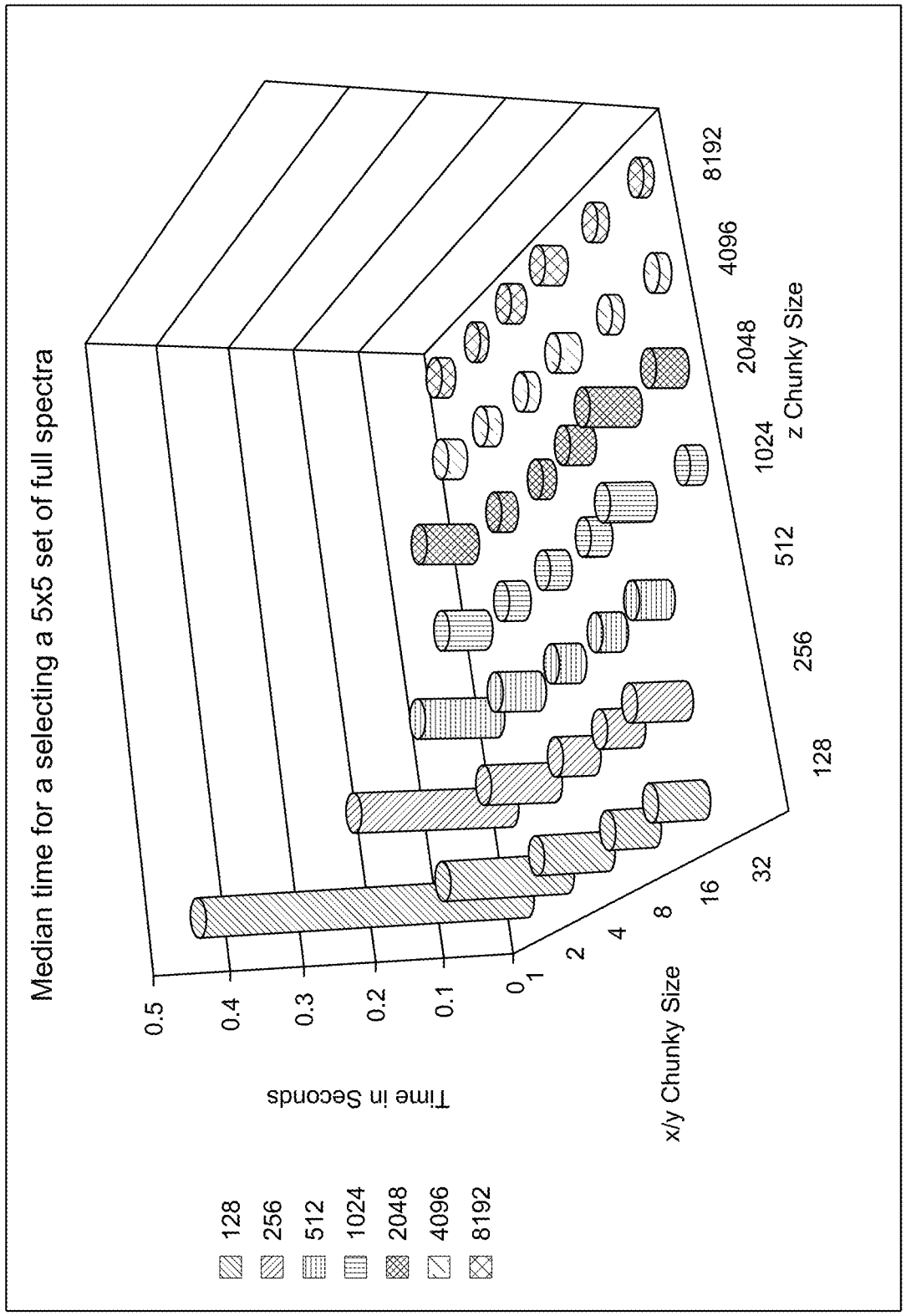
FIG. 14 illustrates, for the read of a random 5×5 subset of full spectra, better read performance for chunked data layouts with larger spatial z chunk sizes is observed.

FIG. 14 illustrates, for the read of a random 5×5 subset of full spectra, better read performance for chunked data layouts with larger spatial z chunk sizes was observed. This behavior is expected as larger z chunk sizes imply that fewer chunks need to be read.

Figure 15:
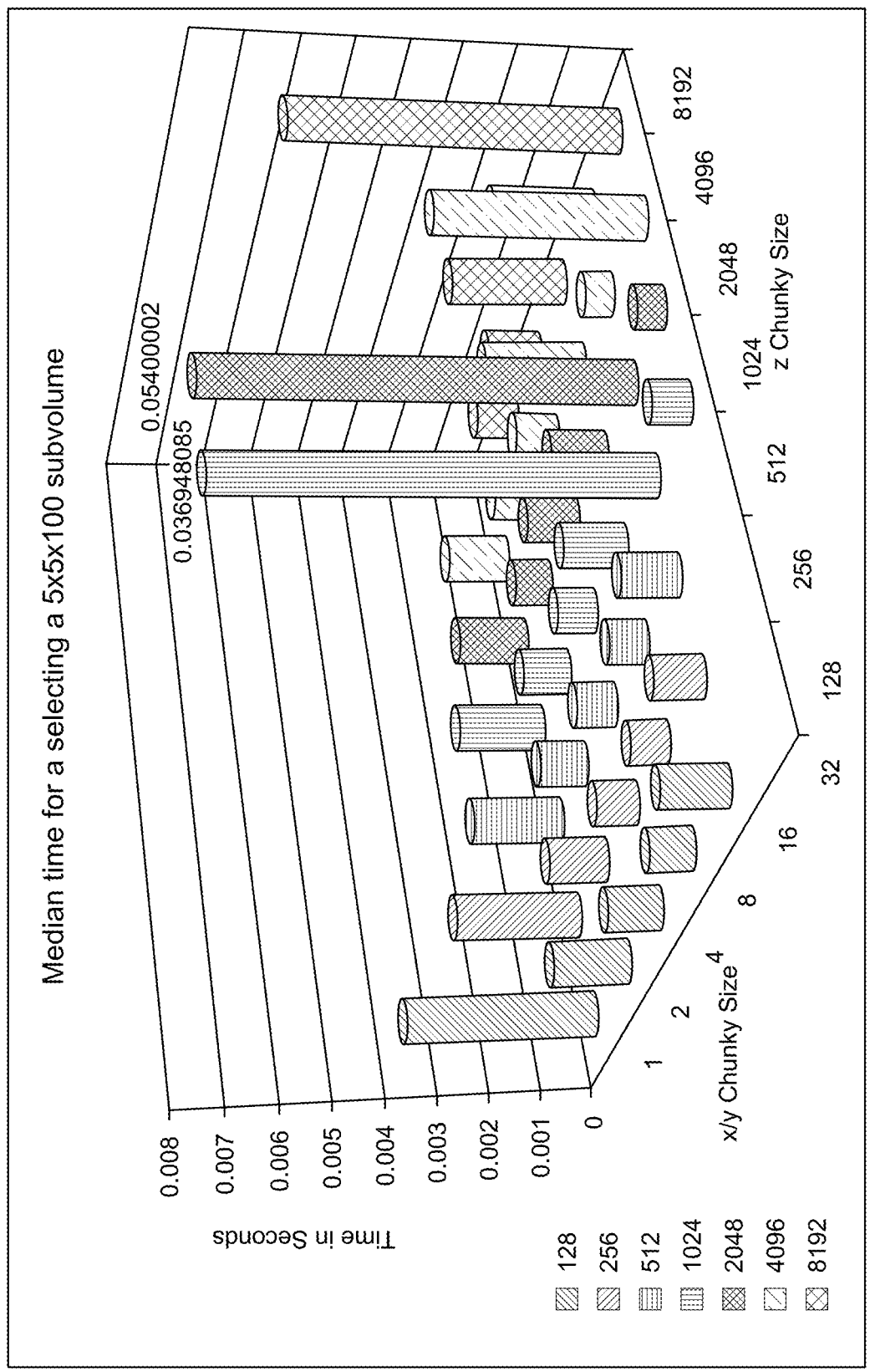
FIG. 15 illustrates the median read performance for the selective read of a random 5×5×100 sub-volumes of the test data.

FIG. 15 illustrates the median read performance for the selective read of a random 5×5×100 sub-volumes of the test data.

Figure 16:
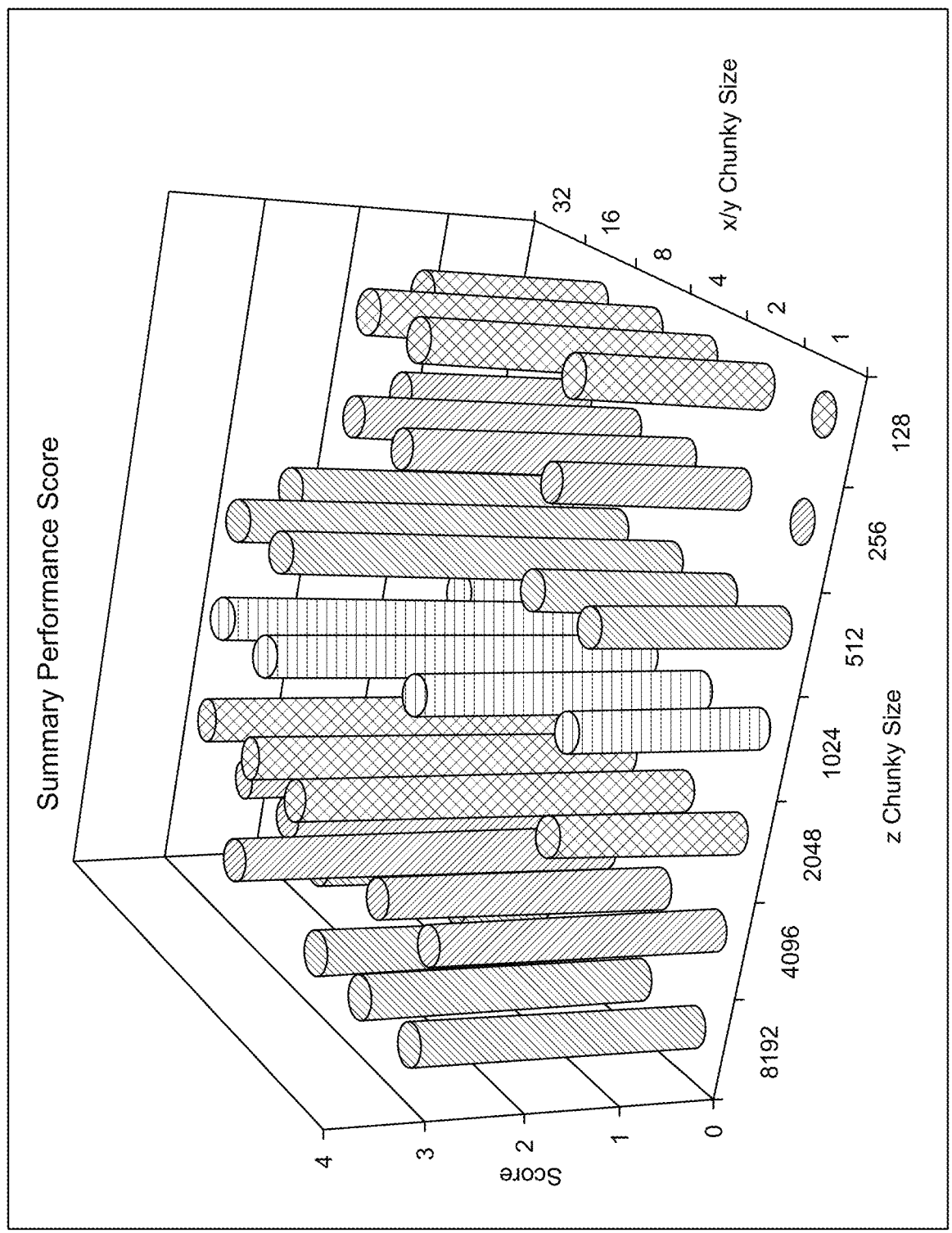
FIG. 16 illustrates the overall performance of the different dataset layouts and to identify the "best" layouts.

FIG. 16 illustrates the overall performance of the different dataset layouts to identify the "best" layouts. In order to do this, the following set of minimum performance criteria a data layout should fulfill was prepared:
  The median time for the z-slice selection test case should be <0.1 s
  The median time for the spectra selection test case should be <0.05 s
  The median time for the 3D subcube selection test case should be <0.002 s
  The total file size should be <2100 MB, limiting the overhead in file size for the test data to a maximum of 200 MB.

Based on these criteria, an overall performance score can be determined by evaluating how many of the criteria a particular data layout fulfills (with 4=best (passes all criteria) and 0=worst (does not pass any of the criteria)). It is observed that a cluster of 8 data layouts satisfies the four performance conditions. Based on these results and experience with real data in practice, a chunked data layout of 4×4×2048 was selected as reference hybrid chunked data layout.

VIII. Application of the OpenMSI System to Other Large-Scale Imaging Data Storage and Analysis In some embodiments, the OpenMSI system may also be configured to store, process, analyze, retrieve, and display data with spectral qualities similar to that obtained from mass spectrometry imaging but from various other sources. For example, the OpenMSI system may be applied to neurosensory data generated by neural recordings; spectroscopic data generated by chromatography that may or may not be coupled to mass spectrometry; spectroscopic data where the spectrum is determined by the wavelength of light being measured; and spectroscopic data where the spectrum is derived from secondary effects such as x-ray photoelectrons. Embodiments of the system may also process, store, analyze, and present all kinds of spectral data or spectroscopy data generated from any spectroscopic method including but not limited to absorption, auger, cavity ring down, circular dichroism, coherent anti-Stokes Raman, cold vapor atomic fluorescence, correlation (several types of 2-dimensional NMR spectroscopy), deep-level transient, dual polarization interferometry, EPR, elastic scattering and reflection, inelastic scattering, inelastic electron tunneling spectroscopy (IETS), emission, energy, force, Fourier transform, frequency, hadron, hyperspectral imaging, Laser-Induced Breakdown Spectroscopy (LIBS), Mossbauer, photoacoustic, photothermal, pump-probe, Raman optical activity, Raman spectroscopy, transmission, reflectance, impedance, resonance (e.g., acoustic resonance), scanning tunneling, spectrophotometry, molecular vibration (e.g. vibrational circulator dichorism), fluorescence, nuclear magnetic resonance, thermal, infrared, atomic force, time-resolved, time-stretch, ultraviolet photoelectron (UPS), X-ray, and/or secondary emission spectroscopic data, etc. Although the raw data formats may be different and the data may have different dimensions, such data can still be stored in data chunks by the OpenMSI system, and the user interface module, storage module, data analysis module, and/or other various modules of the OpenMSI system may still utilize similar systems and methods as described herein to efficiently process and present such data.

IX. Conclusion

Described herein is a system platform that addresses many of the data challenges to storing, retrieving and visualizing large data sets by making advanced, high-performance data analysis and computing easily accessible via the web. The use of the OpenMSI's system's HDF5-based file format was found to be highly suited for this application. Optimization of data layouts using chunking, compression and data replication were found to help enable rapid data access and resulted in more than a 2000-fold improvement in image access to MSI image data and other types of neurosensory data, spectroscopic data, and so forth. The web-based API design enables easy to implement data access patterns with data retrieval speeds of less than 0.3 s across the Internet even for large 50 GB MSI datasets. By making neurosensory data, spectroscopic data, and so forth, easily accessible, without the need for advanced knowledge in high-performance data analysis and computing, OpenMSI promises to transform how MSI and other types of neurosensory and/or spectroscopic techniques are used in practice and promotes the widespread adoption of spectroscopic imaging and neural recordings, such as MSI, as a novel imaging approach.

Having access to neurosensory data, spectroscopic data, and so forth, including, for example, MSI data and neural recording data, and derived analysis via the web browser has shown to be transformative in many ways even in these early stages of the OpenMSI platform, and promises to continue to transform how neurosensory and/or spectroscopic data such as MSI data and/or neural recording data, and so forhtare used. This technology significantly lowers the barrier of entry to using large-scale data, such as neurosensory data, spectroscopic data, and so forth, and allowing even untrained users to interactively explore neurosensory and/or spectroscopic data without the need for assistance of an analysis expert. By having the data accessible through the web browser, scientists can easily share their data and analysis results with collaborators. In other embodiments, the OpenMSI system may also be available through mobile applications, desktop applications, etc., in environments with or without Internet access. Instead of sending a screen shot or a collection of images and spectra, users can share access to data via URLs that capture the interesting observation that needs sharing. Now, when two collaborators are analyzing a file, a URL can be shared that presents the user with an interactive view based on specified parameters. In other embodiments according to this disclosure, capability for propagation of ion identifications to enable community data annotation and improvement of biological interpretation may be added to the OpenMSI system.

In this example, the m/z values and range are specified for creating an RGB image of three distinct ions and the spatial location of two cursors are defined selecting two spectra of interest plotted separately (an example view of the OpenMSI web viewer prototype is shown in herein and also in FIG. 8).

Those having skill in the art will further appreciate that the various illustrative logical blocks, modules, circuits, and process steps described in connection with the implementations disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. One skilled in the art will recognize that a portion, or a part, may comprise something less than, or equal to, a whole. For example, a portion of a collection of pixels may refer to a sub-collection of those pixels.

The various illustrative logical blocks, modules, and circuits described in connection with the implementations disclosed herein may be implemented or performed with a general purpose processor, a digital signal processor (DSP), an application specific integrated circuit (ASIC), a field programmable gate array (FPGA), a graphics processing unit (GPU) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or process described in connection with the implementations disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of non-transitory storage medium known in the art. An exemplary computer-readable storage medium is coupled to the processor such the processor can read information from, and write information to, the computer-readable storage medium. In the alternative, the storage medium may be integral to the processor. The processor and the storage medium may reside in an ASIC. The ASIC may reside in a user terminal, camera, or other device. In the alternative, the processor and the storage medium may reside as discrete components in a user terminal, camera, or other device.

Headings are included herein for reference and to aid in locating various sections. These headings are not intended to limit the scope of the concepts described with respect thereto. Such concepts may have applicability throughout the entire specification.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

APPENDIX

1. An example script for testing local file read performance
2. An example Matlab® script for testing remote read performance are attached as appendices. These documents are incorporated by reference in their entirety for all purposes, and are made a part of this patent application.

Appendix I

Script: For Testing Teal File Read Performance

"""Script for testing the read performance of a set of HDF5 files: The goal is to evaluate the performance of files with different data layouts for the same data. The script performs three main read tests: i) ion-images, ii) spectra, and iii) sub cube: To evaluate the estimated performance in the context of a web-based application, we start a new python interpreter for each data read, execute the read, and close the read process."""

```
from omsi.dataformat.omsi_file import *
import time
import json
import sys
from sys import argv,exit
import numpy as np
import os
import random
import subprocess
def main(argv=None):
    #Check and read input parameters
    if argv is None:
        argv=sys.argv
    if len(argv)<2
    printHelp( )
    exit(0)
    # If we are a slave process, then read the requested data
        subset and exit if len(argv)==8
    infile=argv[1]
    xmin=int(argv[2])
    xmax=int(argv[3])
    ymin=int(argv[4])
    ymax=int(argv[5])
    zmin int(argv[6])
    zmax=int(argv[7])
    start=time.time( )
    d = omsi_file(infile, 'r').get_exp(0).get_msidata(0)
    loaddata=d[xmin:xmax, ymin:ymax, zmin:zmax]
    # content=json.dumps(loaddata.tolist( ))
    stop=(time.time( )-start)
    print stop
    exit(0)
    # if we are the master process then define the test
        parameters
    repeats=50
    outfolder=argv[1]
    filelist=[<list_of_files>]
    # Initalize the output data structures
    data_shapes={ }
    results={ }
    for filename in filelist
    # Initialze data shape
    f=omsi_file(filename, 'r')
    d=f.get_exp(0).get_msidata(0)
    data shapes[filename]=d.shape
    f.close_file( )
    # Initialze output storage
        results[filename]=np.zeros(repeats,     dtype=[('mz-
            slice','f'), ('spectrum','f') , ('xyz-cube','f'), ('mz-
            slice-all','f') , ('spectrum-all','f') , ('xyz-cube-all',
            'f'), ('filesize', 'f')])
    results[filename]['filesize'] = os.stat(filename).st_size
    # Note: We compute each test separately so that we have
        touched # enough data from other files to avoid biases
        due to data cacheing.
```

Note: Depending on the file system, a significant amount of data
  # and in some cases complete files) can be cached by the file
  # system. In particular for small datasets this can result in slow # initial data access and much faster repeated data access during a # given test.

```
# Compute the slice query test
for filename in filelist:
print filename+"25 mz-slices"
# mz-slice selection 250,000 elements
sliceWidthZ=25 # xdim=100 ydim=100
for ri in xrange(0, repeats)
    xmin >0
    xmax=data_shapes[filename] [0]
    ymin=0
    ymax=data_shapes[filename][1]
    zmin=random.randint(0,     data_shapes[filename][2]-
        sliceWidthZ-1)
    zmax=zmin+sliceWidthZ
    callCommand=["python",     "testhdf5_file_read.py",
        filename, str(xmin), str(xmax), str(ymin), str(ymax),
        str(zmin), str(zmax)]
    start=time.time( )
    p2=subprocess.Popen(callCommand,
        stdout=subprocess.PIPE)
    readTime=float(p2.stdout.read( )
    stop=(time.time( )-start)
    results[filename]['mz-slice'][ri]=readTime
    results[filename]['mz-slice-all'][ri]=stop
# Compute the spectra test
for filename in filelist
print filename+"3x3 spectra"
# mz slice selection 250,000 elements
sliceWidthX=3
sliceWidthY=3
for ri in xrange(0, repeats)
    xmin=random.randint(0,     data_shapes[filename][0]-
        sliceWidthX-1)
    xmax=xmin+sliceWidthX
    ymin=random.randint(0,     data_shapes[filename][1]-
        sliceWidthY-1)
    ymax=ymin+sliceWidthY
    zmin=0
    zmax=data_shapes[filename] [2]
    callCommand=["python" "testhdf5_file_read.py", file-
        name, str(xmin), str(xmax), str(ymin), str(ymax),
        str(zmin), str(zmax)]
    start=time.time( )
    p2=subprocess.Popen(callCommand,
        stdout=subprocess.PIPE)
    readTime=float(p2.stdout.read( ))
    stop=(time.time( )-start)
    results[filename]['spectrum'][ri]=readTime
    results[filename]['spectrum-all'][ri]=stop
# Compute the cube test
for filename in filelist:
print filename+"20x20x1000 cube"
# mz-slice selection 250,000 elements
sliceWidthX=20
sliceWidthY=20
sliceWidthZ = 1000
for ri in xrange(0, repeats):
    xmin=random.randint(0,     data_shapes[filename][0]-
        sliceWidthX-1)
    xmax=xmin+sliceWidthX
```

```
    ymin=random.randint(0,    data_shapes[filename][1]-
        sliceWidthY-1)
    ymax=ymin+sliceWidthY
    zmin=random.randint(0,    data_shapes[filename][2]-
        sliceWidthZ-1)
    zmax = zmin+sliceWidthZ
    callCommand=["python",    "testhdf5_file_read.py",
        filename, str(xmin), str(xmax), str(ymin), str(ymax),
        str(zmin), str(zmax)]
    start=time.time( )
    p2              =  subprocess.Popen(callCommand,
        stdout=subprocess.PIPE)
    readTime=float(p2.stdout.read( ))
    stop=(time.time( )-start)
    results[filename]['xyz-cube'][ri]=readTime
    results[filename]['xyz-cube-all'][ri]=stop
# Save the test results to file
for filename in filelist:
    infilename=os.path.split(filename)[1]
    outfile=outfolder+infilename+"_timings.txt"
    f=open(outfile,'w')
    for colName in results[filename].dtype.names:
        f.write(colName+" ")
    f.write("\n")
    np.savetxt(f, results[filename])
    f.close( )
exit(0)
def printHelp( )
""""Print the help explaining the usage of stEIDF5Optim
ion"""""
    print "USAGE: Call \"testhdf5_file_read reSultsFile\""
    print "Execute query: testhdf5_file_read filename xmin
        xmax ymin ymax zmin zmax"
if_name_ == "_main_":
    main( )
```

Appendix II

Matlab® script for testing remote read performance
```
clear all
close all
clc
%%% test cases
clc
N=20000; %this is the number of tests to perform
file{1}='20120711_Brain.h5';
file{2}='2012_0403_KBL_platename.h5';
file{3} =
'20111207_KBL_Roots_BigChip_SmallRoots.h5';
t1=tic
for iii=1:length(file)
    str=
sprintf('https://openmsi.nersc.gov/openmsi/qmetadata/
?file=/data/openmsi/omsi_data/%s&expIn
dex=0&mtype=experimentFull',file{iii})
    [s status]=urlread(str);
    s=loadjson(char(s));
    OutData{iii}.dataShape=s.data_0.shape;
    % dimension an empty martrix to store the time, status,
x-coordinate,
    % and y-coordinate of each spectrum requested from the
server
    OutData{iii}.spectraTimes=zeros(N,4);
    for i=1:size(OutData{iii}.spectraTimes,1)
    idx1=round(rand*(OutData{iii}.dataShape(1)-1));
    idx2=round(rand*(OutData{iii}.dataShape(2)-1));
    str=
sprintf('https://openmsi.nersc.gov/openmsi/qspectrum/
?file=%s&expIndex=0&dataIndex=0&x=%d&y=%d&
findPeaks=0&format=JSON',file{iii},idx1,idx2);
    tic % start the timer
    [s status]=urlread(str);
    t=toc; % stop the timer
    OutData{iii}.spectraTimes(i,1) = t;
    OutData{iii}.spectraTimes(i,2)=status;
    OutData{iii}.spectraTimes(i,3)=idx1;
    OutData{iii}.spectraTimes(i,4)=idx2;
    disp(['Message',num2str(i),'received   in',num2str(spec-
        traTimes(i)),'seconds']);
    end
    % dimension an empty matrix to store the time, status,
minimum m/z, and
    % maximum m/z for each requested image
    Each image is a maximum intensity projection across 10
mass bins
    OutData{iii}.sliceTimes=zeros(N,4);
    for i=1:size(OutData{iii}.sliceTimes,1)
    idx=round(rand*(OutData{iii}.dataShape(3)-50));
    str=
sprintf('https://openmsi.nersc.gov/openmsi/qslice/
?file=%s&expIndex=0&dataIndex=0&z=%d:
%d&format=JSON&reduction=max',file{iii},idx,idx+10);
    tic % start the timer
    [s status]=urlread(str);
    t=toc; % stop the timer
    OutData{iii}.sliceTimes(i,1)=t;
    OutData{iii}.sliceTimes(i,2)=status;
    OutData{iii}.sliceTimes(i,3)=idx;
    OutData{iii}.sliceTimes(i,4)=idx=10;
    disp(['Message',num2str(i),'received         in',num2str
        (OutData{iii}.sliceTimes(i,1)),'seconds']);
    end
end
t2 = toc(t1)
%% Check if any of our tests failed
for i=1:3
    sum(OutData{i}.spectraTimes(:,2)==0)
    sum(OutData{i}.sliceTimes(:,2)==0)
end
%% histogram the results of the timed events
edges=0:1:400; % # milliseconds for binning the data
idx=[1 2 3]
for i=1:length(idx)
    [y x]=hist([OutData{idx(i)}.spectraTimes(:,1)
OutData{idx(i)}.sliceTimes(:,1)]*1000,edges);
    subplot(1,3,i)
    bar(x,y,1)
    xlim([0 max(edges)])
    title(num2str(OutData{idx(i)}.dataShape))
    set(gca,'fontsize',20,'fontweight','bold','linewidth',2,
'fontName','courier'))
    legend('Spectra(single pixel)','Unage(MIP of 10 m/z
bins)')
    xlabel('time (msec)');
    ylabel('# Queries');
end
```

What is claimed is:

1. A system comprising a processor and configured to present spectroscopic data to a user computer, the system comprising:
   an interface to a data storage device configured to store spectroscopic data and associated metadata;
   a first storage module configured to split the spectroscopic data and associated metadata into multiple independently accessible data chunks and store the data chunks as individual spectrally aligned data chunks, image aligned data chunks, or hybrid data chunks in the data storage device by using the interface, wherein the stored data chunks comprise sub-blocks of the spectroscopic data, wherein each data chunk is independently accessible by the system, and wherein each spectrally aligned data chunk comprises a portion of a spectrum, each image aligned data chunk comprises a portion of an ion image and each hybrid data chunk comprises a subset of multiple spectra and ion images; and a user interface module configured to receive a request to display a portion of the spectroscopic data and in response to the request selects one or more independently accessible data chunks that include the requested portion of the spectroscopic data from the data storage device and graphically displays the requested portion of the spectroscopic data to the user computer.

2. The system of claim 1, wherein the spectroscopic data comprises spectra generated by absorption, emission, energy, frequency, reflectance, resonance, molecular vibration, and/or secondary emission.

3. The system of claim 1, wherein the spectroscopic data comprises mass spectrometry imaging data.

4. The system of claim 3, wherein the mass spectrometry imaging data comprises a single spectrum or multiple spectra at a plurality of positions, the mass spectrometry imaging data further comprising spectra of intact molecules and fragments of molecules.

5. The system of claim 3, wherein the mass spectrometry imaging data comprises mass to charge ratio and ion-mobility data.

6. The system of claim 3, wherein the mass spectrometry imaging data comprises 1-dimensional, 2-dimensional, or 3-dimensional spectral imaging data.

7. The system of claim 1, wherein the user interface module is configured to retrieve the plurality of the individual spectrally aligned data chunks, image aligned data chunks, and/or hybrid data chunks independently of each other.

8. The system of claim 3, wherein the user interface module is further configured to receive and process API functions, the API functions including URL patterns for sending one or more of:
 a request to retrieve the associated metadata,
 a request to retrieve information about mass-to-charge (m/z) data,
 a request to retrieve one or more ion images and/or ion image slices,
 a request to retrieve one or more m/z spectra, and
 a request to retrieve arbitrary sub-cubes of the mass spectrometry imaging data.

9. The system of claim 3, wherein the associated metadata comprises mass spectrometry imaging instrument information, sample information, and/or imaging settings.

10. The system of claim 3, wherein the first storage module is further configured to store the data chunks in a self-describing file format comprising descriptions of hierarchy of the mass spectrometry imaging data and type of the mass spectrometry imaging data.

11. The system of claim 10, wherein the self-describing file format is the HDF5 file format.

12. The system of claim 1, wherein the user interface module comprises an array-based user interface configured to retrieve the spectroscopic data independent of whether the data is stored in a 3-dimensional cube format or a reduced data format.

13. The system of claim 1, wherein the spectrally aligned data chunks are configured to store a single full spectrum or a portion of a spectrum per data chunk.

14. The system of claim 1, wherein the image aligned data chunks are configured to store a single full ion-image or a portion of an ion-image per data chunk.

15. The system of claim 1, wherein the hybrid data chunks are configured to store at least a portion of a spectrum and a portion of an ion-image per data chunk.

16. The system of claim 1, wherein the first storage module is further configured to compress the spectroscopic data using compression filters.

17. The system of claim 1, further comprising one or more additional storage modules configured to replicate the spectroscopic data and store two or more copies of the spectroscopic data as data chunks.

18. The system of claim 1, wherein the first storage module is configured to store the spectroscopic data as a 2-dimensional dataset of spectra and one or more index datasets that record relationships between spatial locations and the spectra.

19. The system of claim 1, wherein the system further comprises a data analysis module configured to:
 analyze the spectroscopic data;
 track input parameters and dependencies; and
 in response to receiving a request from the user computer, retracing the analysis performed on the spectroscopic data for purposes of repeating an analysis.

20. The system of claim 19, wherein the data analysis module is further configured to process the stored data chunks, the processing comprising data reduction, dimension reduction, feature detection, and/or clustering on the stored data chunks.

21. The system of claim 20, wherein the data reduction includes one or more of maximum, minimum, average, standard deviation, and variance.

22. A non-transitory computer-readable storage medium comprising computer-executable instructions that when executed direct a computing system to:
 split spectroscopic data and associated metadata into multiple independently accessible data chunks;
 store spectroscopic data and associated metadata as a plurality of individual spectrally aligned data chunks, image aligned data chunks, or hybrid data chunks in a data storage device, wherein the stored data chunks comprise sub-blocks of the spectroscopic data, wherein each data chunk is independently accessible by the computing system, wherein each spectrally aligned data chunk comprises a portion of a spectrum, each image aligned data chunk comprises a portion of an ion image and each hybrid data chunk comprises a subset of multiple spectra and ion images;
 receive a request to display a portion of the spectroscopic data; and
 in response to the request select one or more independently accessible data chunks and graphically display the to requested portion of the spectroscopic data to a user computer.

23. The non-transitory computer-readable storage medium of claim 22, wherein the spectroscopic data comprises spectra generated by absorption, emission, energy, frequency, reflectance, resonance, molecular vibration, and/or secondary emission.

24. The non-transitory computer-readable storage medium of claim 22, wherein the spectroscopic data is mass spectrometry imaging data and in response to receiving instructions from a user computer, retrieving the image slices, spectral data, or arbitrary sub-cubes from the stored data chunks and graphically displaying the retrieved data and the associated metadata to the user computer.

25. The non-transitory computer-readable storage medium of claim 24, wherein the mass spectrometry imaging data comprises multiple spectra at a plurality of positions, the mass spectrometry imaging data further comprising spectra of intact molecules and fragments of molecules.

26. The non-transitory computer-readable storage medium of claim 24, wherein the associated metadata includes mass spectrometry imaging instrument information, sample information, and/or imaging settings.

27. The non-transitory computer-readable storage medium of claim 24, wherein the data chunks are stored in a self-describing file format, the self-describing file format comprises descriptions of hierarchy of the spectroscopic data and type of the spectroscopic data.

28. A computer-implemented method in a computer having a processor, comprising:
obtaining spectroscopic data and associated metadata from an imaging device;
splitting the spectroscopic data and the associated metadata into a plurality of independently accessible data chunks;
storing the spectroscopic data and the associated metadata as a plurality of individual spectrally aligned data chunks, image aligned data chunks, or hybrid data chunks to a data storage device, wherein the stored data chunks comprise sub-blocks of the spectroscopic data, wherein each data chunk is independently accessible by the computer wherein each spectrally aligned data chunk comprises a portion of a spectrum, each image aligned data chunk comprises a portion of an ion image and each hybrid data chunk comprises a subset of multiple spectra and ion images;
receiving a request to display a portion of the spectroscopic data; and
in response to the request selecting one or more independently accessible data chunks that include the requested portion of the spectroscopic data from the data storage device and graphically displaying the requested portion of the spectroscopic data to the user computer.

29. The computer-implemented method of claim 28, wherein obtaining the spectroscopic data comprises obtaining neurosensory and/or spectroscopic data generated by absorption, emission, energy, frequency, reflectance, resonance, molecular vibration, and/or secondary emission.

30. The computer-implemented method of claim 28, wherein obtaining the spectroscopic data comprises obtaining mass spectrometry imaging data from a mass spectrometer.

31. The computer-implemented method of claim 30, wherein obtaining the mass spectrometry imaging data comprises obtaining multiple spectra at a plurality of positions, the mass spectrometry imaging data further comprising spectra of intact molecules and fragments of molecules.

32. The computer-implemented method of claim 28, wherein storing the spectroscopic data comprises storing the spectroscopic data in data chunks in a self-describing file format, the self-describing file format comprising descriptions of hierarchy of the spectroscopic data and type of the spectroscopic data.

33. The computer-implemented method of claim 28, wherein retrieving spectral data further comprises retrieving one or more of the spectrally aligned data chunks, image aligned data chunks, and/or hybrid data chunks independently.

34. The system of claim 1, wherein the first storage module is configured to store the data chunks as both the individual spectrally aligned data chunks and the image aligned data chunks in the data storage device.

35. The system of claim 34, wherein the user interface module is configured to select the one or more individually accessible data chunks from either the spectrally aligned data chunks or the image aligned data chunks based on which is most efficient to resolve the request from the data storage device.

* * * * *